United States Patent [19]

Berger et al.

[11] Patent Number: 5,202,333

[45] Date of Patent: Apr. 13, 1993

[54] TRICYCLIC 5-HT₃ RECEPTOR ANTAGONISTS

[75] Inventors: Jacob Berger, Los Altos Hills; Robin D. Clark, Palo Alto; Richard M. Eglen, Mountain View; William L. Smith, Sunnyvale; Klaus K. Weinhardt, San Francisco, all of Calif.

[73] Assignee: Syntex (U.S.A.) Inc., Palo Alto, Calif.

[21] Appl. No.: 704,565

[22] Filed: May 22, 1991

Related U.S. Application Data

[63] Continuation-in-part of Ser. No. 442,082, Nov. 28, 1989, abandoned.

[51] Int. Cl.⁵ ............... C07D 471/08; A61K 31/55; A61K 31/455
[52] U.S. Cl. ........................ 514/296; 514/211; 514/872; 540/520; 546/99; 546/100
[58] Field of Search .............. 546/99, 100; 540/520; 514/211, 296

[56] References Cited

U.S. PATENT DOCUMENTS

| | | | |
|---|---|---|---|
| 3,341,528 | 9/1967 | Shavel, Jr. | 546/98 |
| 3,896,132 | 7/1975 | Bernauer | 260/289 R |
| 4,309,543 | 1/1982 | Keeley | 546/98 |
| 4,571,396 | 1/1986 | Hutt | 546/156 |
| 4,959,367 | 9/1990 | King et al. | 514/243 |

FOREIGN PATENT DOCUMENTS

| | | |
|---|---|---|
| 0093488 | 11/1983 | European Pat. Off. |
| 430190 | 6/1991 | European Pat. Off. |
| 88-04292 | 6/1988 | World Int. Prop. O. |

OTHER PUBLICATIONS

Reynolds, J. C. 1989, Prokinetic Agents: A Key in the Future of Gastroenterology, Gastroenterology Clinics of North America, 18:437–457.
1989, Drugs Acting on 5-Hydroxytryptamine Receptors, The Lancet, pp. 717–719.
Scholtysik, G. 1988, 5-Hydroxytryptamine Antagonist ICS 205-930 Blocks Cardiac Potassium, Sodium and Calcium Channels, J. of Pharmacol. Exp. Ther. 245, 3:773–778.
King et al. 1990, Benzotriazinones as "Virtual Ring" Mimics of o-Methoxybenzamides: Novel and Potent 5-HT₃ Receptor Antagonists, *J. Med. Chem.* 33:2942–2944.
Peatfield, R. 1988, Drugs and the treatment of Migraine, *Trends Pharmacol. Sci.* 9:141–145.
Komatsu et al. 1978, Chem. Abs. 89:100352x.
Hibert et al. 1988, Preparation and testing of 4-(-2-pyrimidinyl)-1-piperazinepyrimidinediones and -oxazinones as minor tranquilizers, Chem. Abs. 108:221716p.

*Primary Examiner*—Mark L. Berch
*Attorney, Agent, or Firm*—Wayne W. Montgomery; Derek P. Freyberg; Tom M. Moran

[57] ABSTRACT

The present invention is directed to 5-HT₃ receptor antagonist compounds of formula I:

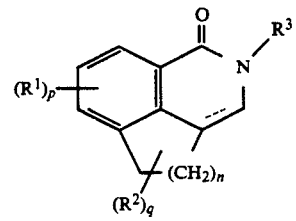

in which
the dashed line denotes an optional double bond;
n is 1, 2 or 3;
p is 0, 1, 2 or 3;
q is 0, 1 or 2;
each $R^1$ is independently selected from halogen, hydroxy, lower alkoxy, lower alkyl, nitro, amino, amino carbonyl, (lower alkyl)amino, di(lower alkyl)amino, and (lower alkanoyl)amino;
each $R^2$ is lower alkyl; and
$R^3$ is a group selected from Formulae (a), (b), (c) and (d):

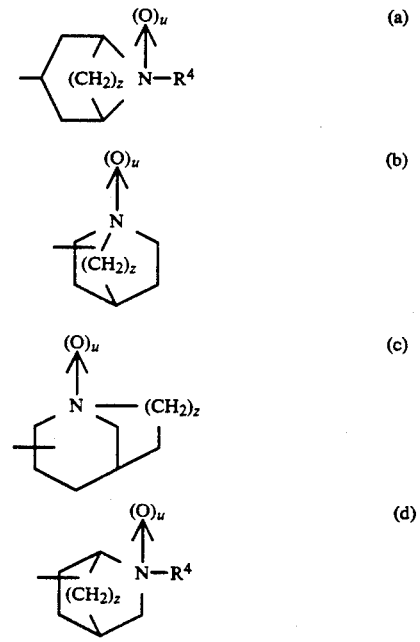

in which
u is 0 or 1;
z is 1, 2 or 3; and
$R^4$ is $C_{1-7}$ alkyl, $C_{3-8}$ cycloalkyl, $C_{3-8}$ cycloalkyl-$C_{1-2}$ alkyl, or a group $(CH_2)_tR^5$ where t is 1 or 2 and $R^5$ is thienyl, pyrrolyl, or furyl, each optionally further substituted by one or two substituents selected from $C_{1-6}$ alkyl, $C_{1-6}$ alkoxy, trifluoromethyl or halogen, or is phenyl optionally substituted by one or two substituents selected from $C_{1-4}$ alkoxy, trifluoromethyl, halogen, nitro, carboxy, esterified carboxy, and $C_{1-4}$ alkyl optionally substituted by hydroxy, $C_{1-4}$ alkoxy, carboxy, esterified carboxy or in vivo hydrolyzable acyloxy; and the pharmaceutically acceptable salts, individual isomers, mixtures of isomers, processes for preparation, compositions, and methods of use thereof.

50 Claims, No Drawings

TRICYCLIC 5-HT₃ RECEPTOR ANTAGONISTS

This application is a continuation-in-part of copending application, Ser. No. 07/442,082, filed Nov. 28, 1989 and now abandoned.

FIELD OF THE INVENTION

This invention relates to novel compounds which are 5-HT$_3$ receptor antagonists, pharmaceutical compositions containing them and methods for their use and methods for preparing these compounds. In particular, it relates to tricyclic 5-HT$_3$ receptor antagonists containing a bridged bicyclic amine substituent. The invention also relates to novel intermediates for making the 5-HT$_3$ receptor antagonists.

BACKGROUND OF THE INVENTION

Serotonin, a neurotransmitter with mixed and complex pharmacological characteristics, was first discovered in 1948 and subsequently has been the subject of substantial research. Serotonin, also referred to as 5-hydroxytryptamine (5-HT), acts both centrally and peripherally on discrete 5-HT receptors. 5-HT Receptors are presently delineated into three major subclassifications - 5-HT$_1$, 5-HT$_2$ and 5-HT$_3$ - each of which may also be heterogeneous. Receptors of the 5-HT$_3$ subclass pervade autonomic neurons and appear to regulate the release of a variety of neurotransmitters in the gastrointestinal, cardiovascular and central nervous systems.

5-HT$_3$ receptors are located in high densities on neurons associated with the emetic reflex and drugs which block the interactions of serotonin at the 5-HT$_3$ receptor level, i.e., 5-HT$_3$ receptor antagonists, possess potent antiemetic properties. Such antagonists demonstrate utility for counteracting the emetic effects of cancer chemotherapy and radiotherapy (see Drugs Acting on 5-Hydroxytryptamine Receptors: *The Lancet* Sep. 23, 1989 and refs. cited therein).

Functional bowel disorders are prevalent in much of the industrialized world. Chronic gastroesophageal reflux disease alone may be present in as much as 15% of the population. Use of prokinetic agents is one of the most effective methods known for treating such disorders. Because many 5-HT$_3$ antagonists possess prokinetic properties and are relatively free from side effects they are particularly useful in the treatment of gastrointestinal diseases (see Reynolds R. C. Prokinetic Agents: A Key in the Future of Gastroenterology. *Gastroenterology Clinics of North America* 1989, 18, 437-457).

5-HT$_3$ receptors are present in those areas of the brain which control mood, emotion, reward and memory. 5-HT$_3$ receptor antagonists reduce mesolimbic dopamine levels, a necessary property for antipsychotic activity. Such antagonists also increase cholinergic tone in the limbic-cortical region, which may explain their cognitive enhancing effects. In addition, 5-HT$_3$ antagonists possess anxiolytic properties, demonstrate potential for use in the treatment of dependency disorders and are under investigation in patients with schizophrenia (see article from *The Lancet* previously cited).

There is evidence that 5-HT$_3$ receptors mediate nociceptive input to afferent neurons (see Glaum, S.; Proudfit, H. K.; Anderson, E. G. *Neurosci. Lett.* 1988, 95, 313). 5-HT$_3$ antagonists may therefore be of value in the control of pain, particularly migraine (see Peatfield R.; Drugs and the Treatment of Migraine. *Trends. Pharmacol. Sci.* 1988, 9, 141).

The 5-HT$_3$ receptor antagonist ICS 205-930 inhibits arrhythmias in a variety of animal models and exerts mixed class III and class I antiarrhythmic properties in ventricular myocytes (see Scholtysik, G.; Imoto, Y.; Yatani, A; Brown, A. M. *J. Pharmacol. Exp. Ther.* 1988, 245, 773 and references therein). 5-HT$_3$ antagonists may therefore be of use in treating or preventing arrhythmias.

The disclosures of these and other documents referred to throughout this application, e.g., in the Pharmacology section of the Detailed Description of the Invention, are incorporated herein by reference.

SUMMARY OF THE INVENTION

The first aspect of this invention is the compounds of Formula I:

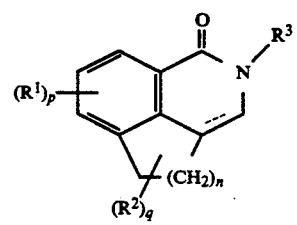

in which
the dashed line denotes an optional double bond;
n is 1, 2 or 3;
p is 0, 1, 2 or 3;
q is 0, 1 or 2;
each R$^1$ is independently selected from halogen, hydroxy, lower alkoxy, lower alkyl, nitro, amino, aminocarbonyl, (lower alkyl)amino, di(lower alkyl)amino, and (lower alkanoyl)amino;
each R$^2$ is lower alkyl; and
R$^3$ is a group selected from Formulae (a), (b), (c) and (d):

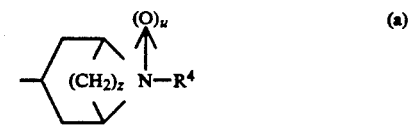
(a)

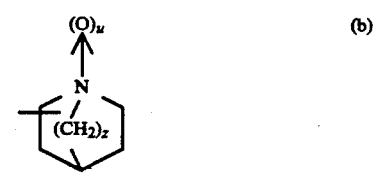
(b)

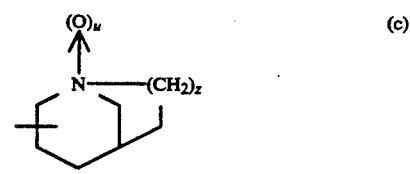
(c)

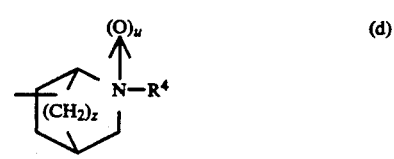
(d)

in which
 u is 0 or 1;
 z is 1, 2 or 3; and
 $R^4$ is $C_{1-7}$ alkyl, $C_{3-8}$ cycloalkyl, $C_{3-8}$ cycloalkyl-$C_{1-2}$ alkyl, or a group $(CH_2)_t R^5$ where t is 1 or 2 and $R^5$ is thienyl, pyrrolyl, or furyl, each optionally substituted by one or two substituents selected from $C_{1-6}$ alkyl, $C_{1-6}$ alkoxy, trifluoromethyl or halogen, or is phenyl optionally substituted by one or two substituents selected from $C_{1-4}$ alkoxy, trifluoromethyl, halogen, nitro, carboxy, esterified carboxy, and $C_{1-4}$ alkyl optionally further substituted by hydroxy, $C_{1-4}$ alkoxy, carboxy, esterified carboxy or in vivo hydrolyzable acyloxy; and the pharmaceutically acceptable salts, individual isomers and mixtures of isomers thereof.

A second aspect of this invention is a pharmaceutical composition containing a compound of Formula I in admixture with one or more suitable excipients.

A third aspect of this invention is a method of treating diseases involving emesis, gastrointestinal disorders, CNS disorders, cardiovascular disorders or pain by administering a therapeutically effective amount of a compound of Formula I to a subject afflicted with such a condition.

A fourth aspect of this invention is the compounds of Formula II:

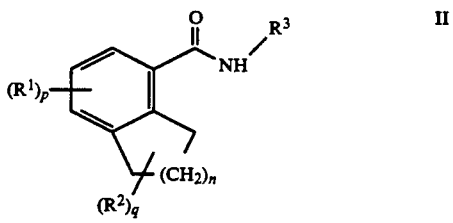

in which n, p, q, $R^1$, $R^2$ and $R^3$ are as defined for Formula I, which are useful intermediates in preparing compounds of Formula I.

A fifth aspect of this invention are the processes for preparing compounds of Formula I and is set forth in the "Detailed Description Of The Invention."

DETAILED DESCRIPTION OF THE INVENTION

Definitions

Unless otherwise stated, the following terms used in the specification and claims have the meanings given below:

"Alkyl" means a straight, branched, or cyclic saturated hydrocarbon radical having from one to the number of carbon atoms designated. For example $C_{1-7}$ alkyl is alkyl having at least one but no more than seven carbon atoms, e.g., methyl, ethyl, i-propyl, n-propyl, n-butyl, cyclopropylmethyl, pentyl, cyclohexyl, heptyl and the like.

"Alkoxy" means the radical —OR wherein R is alkyl having from one to the number of carbon atoms designated, e.g., $C_{1-7}$ alkoxy includes, e.g., methoxy, ethoxy, i-propoxy, n-propoxy, n-butoxy, pentoxy, hexoxy and the like.

"Alkonyl" means the radical —C(O)R wherein R is alkyl having from one to the number of carbon atoms designated, e.g., $C_{1-7}$ alkonyl includes ethanoyl, propanoyl, i-butanoyl, n-butanoyl, pentanoyl, hexanoyl and the like.

"Lower" modifies alkyl, alkoxy and alkonyl and refers to those alkyl radicals or R groups in alkoxy and alkonyl radicals containing 1 to 6 carbon atoms.

"Halogen" means fluorine, chlorine, bromine, or iodine.

"Esterified carboxy" means the ester group —COOR wherein R is $C_{1-8}$ alkyl.

"In vivo hydrolyzable acyloxy" means a group —OC(O)R, wherein R is $C_{1-8}$ alkyl, capable of undergoing enzymatic hydrolysis within a living organism.

"Leaving group" has the meaning conventionally associated with it in synthetic organic chemistry, i.e., an atom or group displaceable under alkylating conditions, and includes halogen and alkane- or arenesulfonyloxy such as mesyloxy, ethanesulfonyloxy, benzenesulfonyloxy, tosyloxy and the like.

"Animal" includes humans, non-human mammals (e.g., dogs, cats, rabbits, cattle, horses, sheep, goats, swine, and deer) and non-mammals (e.g., birds and the like).

"Cytotoxic agents" include platinum anti-cancer agents such as cisplatin (cis-diamminedichloroplatinum), as well as non-platinum anti-cancer drugs such as cyclophosphamide (cytoxin), vincristrine (leurocristine), procarbazine (N-(1-methylethyl)-4-[(2-methylhydrazino)methyl]benzamide), methotrexate, fluorouracil, mechlorethamine hydrochloride (2-chloro-N-(2-chloroethyl)-N-methylethanamine hydrochloride), doxorubicin, adriamycin, dactinomycin (actinomycin-D) cytarabine, carmustine, dacarbazine, and others listed at page 1143 of the *Journal of Clinical Oncology* 1989; 7(8): 1143.

"Disease" specifically includes any unhealthy condition of an animal or part thereof and includes an unhealthy condition which may be caused by, or incident to, medical or veterinary therapy applied to that animal, i.e., the "side effects" of such therapy. Thus, "disease" here includes the emesis caused by therapy with agents having emetogenic side effects, in particular by therapy for cancer, such as chemotherapy with cytotoxic agents and radiotherapy.

"Emesis", for the purposes of this application, will have a meaning that is broader than the normal, dictionary definition and includes not only vomiting, but also nausea and retching.

"Optional" or "optionally" means that the subsequently described event or circumstance may or may not occur, and that the description includes instances where the event or circumstance occurs and instances in which it does not. For example, "optional bond" means that the bond may or may not be present and that the description includes both single bonds and double bonds; "optionally converting a compound of Formula I to a corresponding pharmaceutically acceptable salt" means that the conversion may or may not be carried out in order for the process described to fall within the invention, and the invention includes those processes wherein the compound of Formula I is converted to the salt and those processes in which it is not.

"Pharmaceutically acceptable" means that which is useful in preparing a pharmaceutical composition that is generally safe, non-toxic and neither biologically nor otherwise undesirable and includes that which is acceptable for veterinary use as well as human pharmaceutical use.

"Pharmaceutically acceptable salts" means salts which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as acetic acid, propionic acid, hexanoic acid, heptanoic acid, cyclopentanepropionic acid, glycolic acid, pyruvic acid, lactic acid, malonic acid, succinic acid, malic acid, maleic acid, fumaric acid, tartaric acid, citric acid, benzoic acid, o-(4-hydroxybenzoyl)benzoic acid, cinnamic acid, mandelic acid, methanesulfonic acid, ethanesulfonic acid, 1,2,-ethanedisulfonic acid, 2-hydroxyethanesulfonic acid, benzenesulfonic acid p-chlorobenzenesulfonic acid, 2-naphthalenesulfonic acid, p-toluenesulfonic acid, camphorsulfonic acid, 4-methylbicyclo[2.2.-2]oct-2-ene-1-carboxylic acid, glucoheptonic acid, 4,4'-methylenebis(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like.

In addition, pharmaceutically acceptable salts may be formed when an acidic proton present is capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like.

"Therapeutically effective amount" means that amount which, when administered to an animal for treating a disease, is sufficient to effect such treatment for the disease.

"Treating" or "treatment" of a disease includes:
(1) preventing the disease from occurring in an animal which may be predisposed to the disease but does not yet experience or display symptoms of the disease,
(2) inhibiting the disease, i.e., arresting its development, or
(3) relieving the disease, i.e., causing regression of the disease.

Compounds that have identical molecular formulae but differ in the nature or sequence of bonding of their atoms or in the arrangement of their atoms in space are termed "isomers". Isomers that differ in the nature or sequence of bonding of their atoms are termed "constitutional isomers". Isomers that differ only in the arrangement of their atoms in space are termed "stereoisomers". Stereoisomers that are not mirror images of one another are termed "diasteromers" and stereoisomers that are mirror images are termed "enantiomers" or sometimes "optical isomers". Stereoisomers that are superimposable upon their mirror images are termed "achiral" and those not superimposable are termed "chrial". A carbon atom bonded to four different groups is termed a "chiral center" or alternatively an "asymmetric carbon".

When a compound has a chiral center, a pair of enantiomers of opposite chirality is possible. An enantiomer can be characterized by the absolute configuration of its chiral center and described by the R- and S-sequencing rules of Cahn and Prelog (i.e., as (R)- and (S)-isomers) or by the manner in which the molecule rotates the plane of polarized light and designated as dextrorotatory or levorotatory (i.e., as (+)- and (−)-isomers, respectively). A chiral compound can exist as either individual enantiomer or as a mixture thereof. A mixture containing equal proportions of the enantiomers is termed a "racemic mixture" or "racemate" and may be described as the (RS)- or (±)-mixture thereof. Unless indicated otherwise, the description or naming of a particular compound in the specification and claims is intended to include both individual enantiomers and mixtures, racemic or otherwise, thereof. Conventions for stereochemical nomenclature, methods for the determination of stereochemistry and the separation of stereoisomers are well-known in the art (see discussion in Chapter 4 of "Advanced Organic Chemistry", 3rd edition March, Jerry, John Wiley and Sons, New York, 1985).

Certain compounds of Formulae I and II can exist as stereoisomers. For example, certain compounds possess a chiral center at the ring carbon of the $R^3$ substituent which is bonded to the amide nitrogen and, when the optional bond is absent, at the 3a-position and therefore can exist as (R)- or (S)-isomers. In addition, certain compounds can exist as the (endo)- or (exo)-isomers, e.g., when the $R^3$ substituent is 1-azabicyclo[3.3.1]non-4-yl.

When a compound of Formula I or II possesses one chiral center, a pair of enantiomers exists. When two chiral centers are present in a compound of Formula I, four separate steroisomers exist (i.e., two separate pairs of enantiomers). When a compound of Formula I possesses two chiral centers and can exist as endo or exo, eight separate stereoisomers are possible (i.e., two separate pairs of enantiomers in the endo or exo form).

It is to be understood that when referring to Formula I, II, (a), (b), (c) or (d) in this application, a straight line depicting the covalent bond between the $R^3$ substituent and the amide nitrogen represents the possible geometric isomers and enantiomers or the mixtures, racemic or otherwise, thereof. Similarly, when referring to Formula I in which the optionally bond is absent, a straight line depicting the covalent bond between carbons 3a and 4 represents either the R or S configurations or a mixture racemic, or otherwise, thereof. For purposes of the present application when referring to a compound by name or by formula and the configuration is not designated, it is to be understood that the reference is to all possible forms.

Certain $R^3$ substituents described in this application are of particular interest and are therefore defined specifically as the following:

(1) Formula (b) where z is 2 and u is 0 having the specific formula

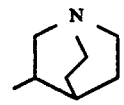

is referred to as 1-azabicyclo[2.2.2]oct-3-yl;

(2) Formula (b) where z is 2 and u is 0 having the specific formula

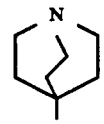

is referred to as 1-azabicyclo[2.2.2]oct-4yl;

(3) Formula (a) where z is 3, u is 0 and $R^4$ is methyl having the specific formula

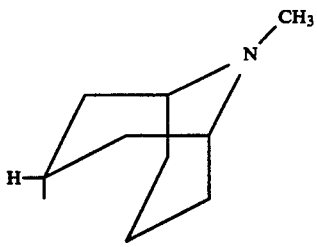

is referred to as (endo)-9-methyl-9-azabicyclo[3.3.1]-non-3-yl;

(4) Formula (a) where z is 3, u is 0 and $R^4$ is methyl having the specific formula

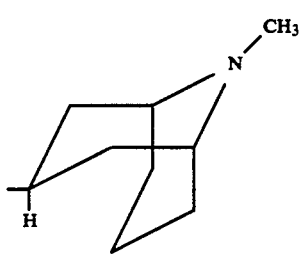

is referred to as (exo)-9-methyl-9-azabicyclo[3.3.1]non-3-yl;

(5) Formula (a) where z is 2, u is 0 and $R^4$ is methyl having the specific formula

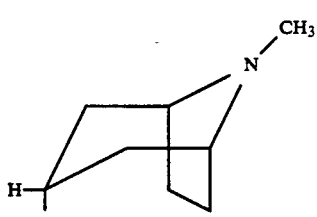

is refered to as (endo)-8-methyl-8-azabicyclo[3.2.1]oct-3-yl;

(6) Formula (a) where z is 2 u is 0 and $R^4$ is methyl having the specific formula

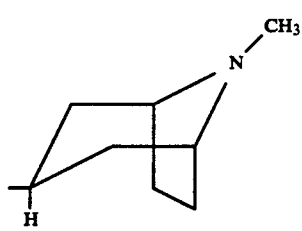

is referred to as (exo)-8-methyl-8-azabicyclo[3.2.1]oct-3-yl;

(7) Formula (c) wherein z is 2 and u is 0 having the specific formula

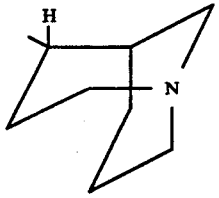

is referred to as (endo)-1-azabicyclo[3.3.1]non-4-yl.

(8) Formula (c) wherein z is 2 and u is 0 having the specific formula

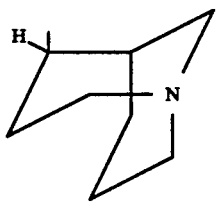

is referred to as (exo)-1-azabicyclo[3.3.1]non-4-yl.

Compounds of Formulae I and II are named in accordance with generally acceptable nomenclature rules established by "Chemical Abstracts." For example, the compound of Formula I in which the optional bond is present, p, q and u are 0 and $R^3$ is 1-azabicyclo-[2.2.2]oct-4-yl:

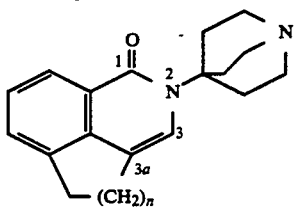

is named
2-(1-azabicyclo[2.2.2]oct-4-yl)-1,2,4,5-tetrahydrocyclopent[de]isoquinolin-1-one when n is 1;
2-(1-azabicyclo[2.2.2]oct-4-yl)-2,4,5,6-tetrahydro-1H-benz[de]isoquinolin-1-one when n is 2; and
2-(azabiyclo[2.2.2]oct-4-yl)-1,2,4,5,6,7-hexahydrocyclohept[de]isoquinolin-1-one when n is 3.

The compound of Formula II in which the optional bond is present, p, q and u are 0 and $R^3$ is 1-azabicyclo-[2.2.2]oct-4-yl:

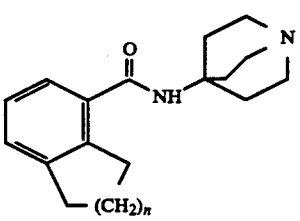

is named
N-(1-azabioyclo[2.2.2]oct-4-yl)-4-indancarboxamide when n is 1;
N-(1-azabicyclo[2.2.2]oct-4-yl)-5,6,7,8-tetrahydro-1-naphthalenecarboxamide when n is 2; and N-(1-azabicyclo[2.2.2]oct-4-yl)-5,6,7,8-tetrahydro-9H-benzocyclohepten-1-carboxamide when n is 3.

PRESENTLY PREFERRED EMBODIMENTS

While the broadest definition of this invention is set forth in the Summary of the Invention, certain compounds of Formulae I and II are preferred. For example, preferred compounds of Formula I are those in which both q and u are 0, p is 1, or 2, each $R^1$ is independently selected from halogen, lower alkoxy or amino, and $R^4$ is lower alkyl.

Of particular interest are those compounds of Formula I in which each p, q and u are 0, $R^4$ is methyl, and $R^3$ is one of the following groups:
1-azabicyclo[2.2.2]oct-3-yl;
1-azabicyclo-[2.2.2]oct-4-yl;
endo-9-methyl-9-azabicyclo[3.3.1]non-3-yl;
exo-9-methyl-9-azabicyclo[3.3.1]non-3-yl;
endo-8-methyl-8-azabicyclo[3.2.1]oct-3-yl;
exo-8-methyl-8-azabicyclo[3.2.1]oct-3-yl;
endo-1-azabicyclo[3.3.1]non-4-yl; or
exo-1-azabicyclo[3.3.1]non-4-yl.

Of most interest are the compounds of Formula I in which each p, q and u are 0, and $R^3$ is 1-azabicyclo[2.2.2]oct-3-yl, in particular wherein one or, when present, both chiral centers possess S configurations.

Preferred compounds of Formula II are those in which both p and q are 0, p is 0, 1, or 2, each $R^1$ is independently selected from halogen, lower alkoxy or amino, and $R^4$ is lower alkyl.

Of particular interest are those compounds of Formula II in which each p, q, and u are 0, $R^4$ is methyl, and $R^3$ is one of the following groups:
1-azabicyclo[2.2.2]oct-3-yl;
1-azabicyclo-[2.2.2]oct-4-yl;
endo-9-methyl-9-azabicyclo[3.3.1]non-3-yl;
exo-9-methyl-9-azabicyclo[3.3.1]non-3-yl;
endo-8-methyl-8-azabicyclo[3.2.1]oct-3-yl;
exo-8-methyl-8-azabicyclo[3.2.1]oct-3-yl;
endo-1-azabicyclo[3.3.1]non-4-yl; or
exo-1-azabicyclo[3.3.1]non-4-yl.

Of most interest are compounds of Formula II in which each p, q, and u are 0, and $R^3$ is 1-azabicyclo[2.2.2]oct-3-yl, in particular the S-isomers thereof.

It is understood that these compounds of Formula II of special interest are particularly useful in the synthesis of preferred compounds of Formula I.

UTILITY

Compounds of Formula I exhibit utility in treating a broad range of diseases in animals, particularly humans. Examples of diseases that may be treated using the compounds of Formula I include emesis, gastrointestinal disorders, central nervous system (CNS) disorders, cardiovascular disorders or pain.

Compounds of Formula I are useful in the prevention and treatment of emesis. Causes of such emesis include surgical anesthesia, psychological stress, pregnancy, certain disease states, radiotherapy, radiation poisoning and toxic substances. Disease states which are known to induce emesis include conditions such as gut obstruction, raised intracranial pressure, acute myocardial infarction, migraine headaches and adrenal crisis. Toxic substances which induce emesis include toxins in the form of abnormal metabolites or abnormal accumulation of natural occurring substances associated with such conditions as hepatic coma, renal failure, diabetic ketoacidosis, hyperthyroid crisis, both hypo- and hyperparathyroidism and Addison's disease. Emesis may also be caused by ingested toxins, e.g., enterotoxins in staphylococcus-contaminated foods, or by drugs administered for therapeutic purposes, e.g., digitalis, emetine and chemotherapeutic agents.

Compounds of Formula I are of particular value in treating (especially preventing) the emesis induced by radiation poisoning, treatment for cancer with radiotherapy or chemotherapy with cytotoxic agents or drug therapy in general wherein a significant side effect is emesis, e.g., amphotericin B in treating immunosuppressed patients, zidovudine (AZT) in the treatment of AIDS and interleukin in treating cancer.

Compounds of Formula I are useful as prokinetic agents in the treatment of gastrointestinal diseases, i.e., diseases of the stomach, esophagus and of both the large and small intestines. Examples of specific diseases include, but are not limited to, dyspepsia (e.g., non-ulcer dyspepsia), gastric stasis, peptic ulcer, reflux esophagitis, flatulence, bile reflux gastritis, pseudo-obstruction syndrome, irritable colon syndrome (which may result in chronic constipation and diarrhea), diverticular disease, biliary dysmotility (which may result in sphincter of Oddi dysfunction and "sludge" or microscopic crystals in the gall bladder), gastroparesis (e.g., diabetic, postsurgical or idiopathic), irritable bowel syndrome amd retarded gastric emptying. The compounds of Formula I are also useful as short-term prokinetics to facilitate diagnostic radiology and intestinal intubation. In addition, the compounds are useful for treating diarrhea, particularly diarrhea induced by cholera and carcinoid syndrome.

Compounds of Formula I are useful in treating diseases of the central nervous system. Categories of such diseases include cognitive disorders, psychoses, obsessive/compulsive and anxiety/depression behavior. Cognitive disorders include attentional or memory deficit, dementia states (including senile dementia of the Alzheimer's type and aging), cerebral vascular deficiency and Parkinson's disease. Psychoses that are treatable using the compounds of Formula I include paranoia, schizophrenia and autism. Obsessive/compulsive behavior that is treatable using compounds of Formula I includes eating disorders, e.g., bulimia, a condition in which an abnormal and constant craving for food is present.

Representative, treatable anxiety/depressive states include anticipatory anxiety (e.g., prior to surgery, dental work, etc.), depression, mania, seasonal affective disorder (SAD), and the convulsions and anxiety caused by withdrawal from addictive substances such as opiates, benzodiazepines, nicotine, alcohol, cocaine and other drugs of abuse.

Compounds of Formula I are useful in the treatment of cardiovascular diseases. Such diseases include arrhythmias and hypertension.

It is thought that 5-$HT_3$ antagonists prevent certain adverse nervous transmissions and/or prevent vasodilation and are therefore of value for reducing perceived levels of pain. Compounds of Formula I are, therefore, useful in treating pain such as that associated with cluster headaches, migraines, trigeminal neuralgia and visceral pain (e.g., that caused by abnormal distension of hollow visceral organs).

In summary, an aspect of this invention is a method for treating an animal, particularly a human, exhibiting a disease involving emesis, a gastrointestinal disorder, a CNS disorders, a cardiovascular disorder or pain by administering a therapeutically effective amount of a compound of Formula I to such animal.

Pharmacology

5-HT$_3$ Receptor binding affinity is measured at 5-HT$_3$ receptors in membranes prepared from the cerebral cortex of rat brains, an accepted in vitro assay (e.g., see Kilpatrick, G. J.; Jones, B. J.; Tyers, M. B. *Nature* 1987, 330, 24–31). The 5-HT$_3$ receptor binding assay is described in Example 14. The compounds of Formula I exhibit affinity for the 5-HT$_3$ receptor in this assay.

5-HT$_3$ receptor antagonist activity is measured by the ability of compounds to inhibit the von Bezold-Jarisch reflex in anesthetized rats, an accepted in vivo assay (e.g., see Butler, A.; Hill, J. M.; Ireland, S. J.; Jordan, C. C.; Tylers, M. B. *Brit. J. Pharmacol.* 1988, 94, 397–412; Cohen, M. L.; Bloomquist, W.; Gidda, J. S.; Lacefield, W. *J. Pharmacol. Exp. Ther.* 1989; 248, 197–201; Fozard, J. R. *Arch. Pharmacol.* 1984, 326, 36–44). The 5-HT$_3$ receptor antagonist assay is described in Example 15.

Anti-emetic activity is determined by measuring reduction of cisplatin-induced emesis in ferrets, an accepted assay (e.g., Costall, B.; Domeney, A. M.; Naylor, R. J.; Tattersall, F. D. *Neuropharmacology* 1986, 25(8), 959–961; Miner, W. D.; Sanger G. J. *Brit. J. Pharmacol.* 1986, 88, 497–499). The ferret, anti-emetic assay is described in Example 16.

Anti-emetic activity is also determined by measuring reduction of cisplatin-induced emesis in dogs, an accepted assay (e.g., see Smith, W. L.; Alphin, R. S.; Jackson, C. B.; Sancilio, L. F. *J. Pharm. Pharmacol.* 1989, 41, 101–105; Gylys, J. A. *Res. Commun. Chem. Pathol. Pharmacol.* 1979, 23(1), 61–68). The dog, anti-emetic assay is described in Example 17.

Prokinetic activity is determined by measuring the rate of gastric emptying after oral administration of test meal to rats, an accepted in vivo assay (e.g., see Droppleman, D.; Gregory, R.; Alphin, R. S. *J. Pharmacol. Methods* 1980, 4(3), 227–30). The prokinetic assay is described in Example 18.

Anxiolytic activity is determined by the art-recognized Crawley and Goodwin two-compartment exploratory model (e.g., see Kilfoil, T.; Michel, A.; Montgomery, D.; Whiting, R. L.; *Neuropharmacology* 1989, 28(9), 901–905). In brief, the method involves determining whether a compound reduces the natural anxiety of mice in a novel, brightly lighted area. The anxiolytic behavior assay is described in Example 19.

Anxiolytic activity during withdrawal from drugs of abuse is determined by the mouse, withdrawal anxiety test, an accepted assay (e.g., see Carboni, E.;, Acquas, E.; Leone, P.; Perezzani, L.; Di Chiara, G. *Eur. J. Pharmacol* 1988, 151, 159–160). This procedure utilizes the exploratory model described above to test for anxiolytic activity after chronic administration and subsequent abrupt cessation of ethanol, diazepam, cocaine or nicotine treatments. The withdrawal anxiety assay is described in Example 20.

Cognition enhancing activity is determined by the mouse, habituation/cognitive enhancement test (e.g., see Barnes, J. M.; Costall, B.; Kelly, M. E.; Naylor, F. J.; Onaivi, E. S.; Tomkins, D. M.; Tyers, M. B. *Br. J. Pharmacol.* 1989, 98, 693P). This procedure utilizes the exploratory model described above to test for improvements in the impaired cognitive performance of aged mice. The cognitive enhancement assay is described in Example 21.

Administration and Pharmaceutical Composition

In general, compounds of Formula I will be administered in therapeutically effective amounts via any of the usual and acceptable modes known in the art, either singly or in combination with another compound of Formula I or with another therapeutic agent. A therapeutically effective amount may vary widely depending on the severity of the disease, the age and relative health of the subject, the potency of the compound used and other factors. Therapeutically effective amounts of compounds of Formula I may range from approximately 1.0 nanogram per Kg (ng/Kg) body weight per day to 1.0 mg/Kg body weight per day. Preferably the amount will be approximately 10 ng/Kg/day to 0.1 mg/Kg/day. Therefore, a therapeutically effective amount for a 70 Kg human may range from 70 ng/day to 70 mg/day, preferably 700 ng/day to 7.0 mg/day.

One of ordinary skill in the art of treating such diseases will be able, without undue experimentation and in reliance upon personal knowledge and the disclosure of this application, to ascertain a therapeutically effective amount of a compound of Formula I for a given disease.

In general, compounds of Formula I will be administered as pharmaceutical compositions by one of the following routes: oral, systemic (e.g., transdermal, intranasal or by suppository) or parenteral (e.g., intramuscular, intravenous or subcutaneous). Compositions can take the form of tablets, pills, capsules, semisolids, powders, sustained release formulations, solutions, suspensions, elixirs, aerosols, or any other appropriate composition and are comprised of, in general, a compound of Formula I in combination with at least one pharmaceutically acceptable excipient. Acceptable excipients are non-toxic, aid administration, and do not adversely affect the therapeutic benefit of the compound of Formula I. Such excipient may be any solid, liquid, semisolid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk, and the like. Liquid and semisolid excipients may be selected from water, ethanol, glycerol, propylene glycol and various oils, including those of petroleum, animal, vegetable or synthetic origin (e.g., peanut oil, soybean oil, mineral oil, sesame oil, etc.). Preferred liquid carriers, particularly for injectable solutions, include water, saline, aqueous dextrose and glycols.

Compressed gases may be used to disperse the compound of Formula I in aerosol form. Inert gases suitable for this purpose are nitrogen, carbon dioxide, nitrous oxide, etc. Other suitable pharmaceutical carriers and their formulations are described in A. R. Alfonso 1985. Reminton's Pharmaceutical Sciences. 17th ed. Easton, Pa.: Mack Publishing Company.

The amount of a compound of Formula I in the composition may vary widely depending upon the type of formulation, size of a unit dosage, kind of excipients and other factors known to those of skill in the art of pharmaceutical sciences. In general, the final composition will comprise from 0.000001% w to 10.0% w of the compound of Formula I, preferably 0.00001% w to 1.0% w, with the remainder being the excipient or excipients.

Preferably the pharmaceutical composition is administered in a single unit dosage form for continuous treatment or in a single unit dosage form ad libitum when relief of symptoms is specifically required. Representative pharmaceutical formulations containing a compound of Formula I are described in Example 13.

Processes for Preparing Compounds of the Invention

Compounds of Formula I are prepared by the reaction sequence shown below in Reaction Scheme I.

SCHEME I

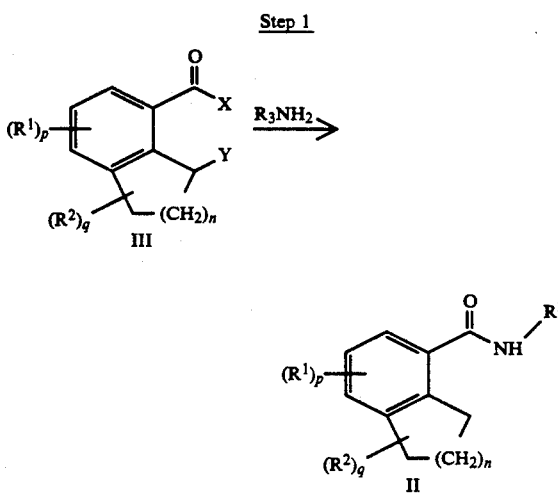

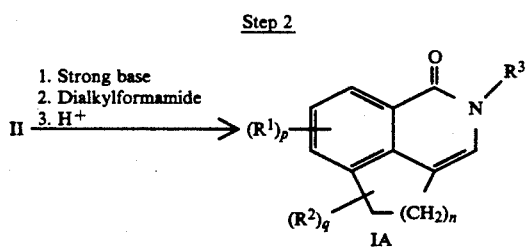

Step 3

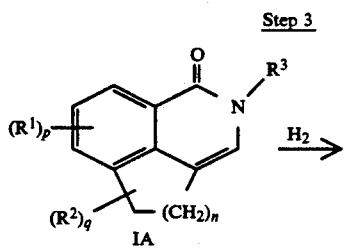

-continued
SCHEME I

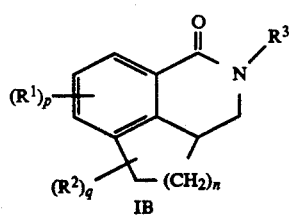

in which X is hydroxy, alkoxy or halogen and Y is hydrogen or X and Y together are oxa, and n, p, q, $R^1$, $R^2$ and $R^3$ are as defined in the Summary of the Invention with the processes applying particularly well to the presently preferred embodiments.

Scheme I

Compounds of Formula I are conveniently prepared by a two step synthesis comprising (1) converting an acid or acid derivative of Formula III or a fused-ring bicyclic compound of Formula VI to a substituted amide of Formula II and (2) reacting the amide with a formylating agent in the presence of a strong base and then acidifying to form a compound of Formula IA (a compound of Formula I in which the optional bond is present). Compounds of Formula IB (compounds of Formula I in which the optional bond is absent) are subsequently prepared by reduction.

Step 1

Compounds of Formula II are prepared by reacting a compound of Formula III with a substituted amine of the formula $NH_2R^3$ in which $R^3$ is as defined in the Summary of the Invention. Reaction conditions are those standard for amide formation (e.g., see J. Advanced Organic Synthesis March 1985, 3rd Ed., 370–376). Generally the reaction is carried out at 20° C. to 200° C., preferably −10° C. to 20° C., and ambient pressure for 0.5 to 3 hours in a suitable inert organic solvent (e.g., methylene chloride, THF and toluene). The conversion of a compound of Formula III in which X is ethoxy to the corresponding amide of Formula II is described in Example 2. The conversion of a compound of Formula III in which X is hydroxy to the corresponding amide of Formula II is described in Example 3. The conversion of a compound of Formula III in which X and Y together are oxo to the corresponding amide of Formula II is described in Example 5.

Alternatively, compounds of Formula II may be prepared by Friedel-Crafts acylation in which a chloroformamide of the formula $ClC(O)NHR^2$ is reacted with a compound of Formula VI in the presence of a Lewis acid such as aluminum chloride, boron trifluoride, hydrogen fluoride or phosphoric acid.

In general, the starting materials utilized in the preparation of compounds of Formula II are known to or can readily be synthesized by those of ordinary skill in the art. For example, the compounds of Formula III where X is hydroxy, p is 1, $R^1$ is methoxy (particularly meta to the acid), q is 0 and n is 1 or 2 are discussed by Lowenthal, H. J.; Schatzmiller, S. J. Chem. Soc. Perkin Trans. I 1976, 944. Unsubstituted compounds (i.e., wherein p and q are both 0) in which n is 1, 2 or 3 are readily available or may be prepared in accordance with methods known in the art.

Compounds of Formula III wherein X and Y are together oxa and n is 1, 2 or 3 can be prepared from an alcohol of the formula

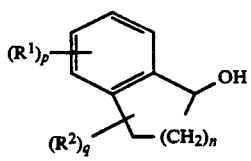

in which n, p, q, $R^1$ and $R^2$ are as defined in the Summary of the Invention by treating with a strong base (e.g., n-butyllithium) in an inert organic solvent (e.g., hexanes) for approximately 20 hours followed by bubbling through with carbon dioxide for approximately 5 hours. The preparation of a compound of Formula III in which X and Y together are oxa is described in Example 1.

Other starting materials that are useful for preparing compounds of the invention are 1-cyano-4-alkoxynaphthalenes which can be hydrolyzed and reduced to the corresponding starting acid of Formula III wherein X is hydroxy, R is 4-alkoxy, q is 0 and n is 2. Halogen-substituted tetralones are well known and are prepared from o-halophenylbutyric acids. These tetralones can be reduced to the appropriate alcohol, converted to an acid and reacted with the $R^3NH_2$ compound as a lactone to form an amide of Formula II.

Step 2

Compounds of Formula IA are prepared by reacting amides of Formula II with a dialkylformamide in the presence of a strong base and than acidifying. The reaction is carried out in a inert ethereal solvent (e.g., diethyl ether, dimethoxyethane or tetrahydrofuran (THF), preferably THF) at temperatures ranging from −70° C. to 25° C., preferably −20° C. to 0° C., at ambient pressure and under an inert atmosphere (e.g., argon or nitrogen, preferably nitrogen). The dialkylformamide, preferably dimethylformamide (DMF), is generally used in molar excess relative to the amide of Formula II. Any strong base, such as a Grignard reagent or an appropriate alkyllithium, preferably n-butyllithium, can be utilized. Step 2 of Scheme I is described in Examples 6, 7, 8 and 9.

Compounds of Formula IB may be prepared by reduction of the corresponding compound of Formula IA. The reduction is carried out under standard hydrogenation conditions with an appropriate hydrogenation catalyst and in a suitable polar, organic solvent. Reaction pressures may vary from atmospheric to approximately 15 megaPascals (mPa) and temperatures may range from ambient to approximately 100° C. While any standard catalyst (e.g., rhodium on alumina, etc.) may be used, certain catalysts are preferred. Preferred catalysts include 10% palladium hydroxide, 20% palladium hydroxide on carbon, Pearlman's catalyst (50% $H_2O$−20% palladium content) and palladium/$BaSO_4$. Suitable solvents include ethanol, DMF, acetic acid, ethyl acetate, tetrahydrofuran, toluene, and the like.

Depending upon the catalyst, solvent, pressure and temperature chosen, the reduction process may take from a few hours to a few days to complete. As an example, a reaction carried out with 20% palladium hydroxide in acetic acid and 70% perchloric acid at 15 kPa and 85° C. takes approximately 24 hours for full reduction to occur. The reduction of a compound of Formula IA to a compound of Formula IB is described in detail in Example 10.

A compound of Formula IA can be reduced in either the nonsalt or salt form. If an optically active reagent is employed to form the salt of a compound of Formula IA, formation of one enantiomer over the other may be favored.

Compounds of Formula I are also prepared by the reaction sequence shown below in Scheme II.

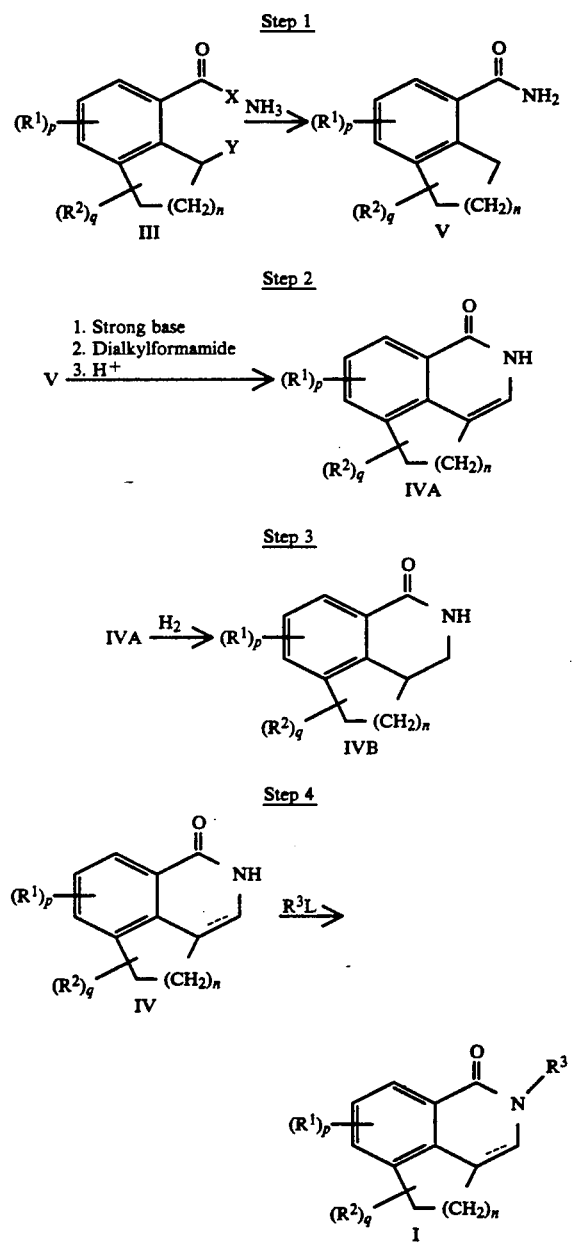

in which X is hydroxy, alkoxy or halogen and Y is hydrogen or X and Y together are oxa, L is a leaving group and n, p, q, $R^1$, $R^2$ and $R^3$ are as defined in the Summary of the Invention, with the processes applying particularly well to the presently preferred embodiments.

Scheme II

Alternatively, compounds of Formula I are prepared by a three step synthesis comprising (1) converting an acid or acid derivative of Formula III to an unsubstituted amide of Formula V, (2) reacting the amide with a formylating agent in the presence of a strong base and then acidifying to form a compound Formula IVA (a compound of Formula IV in which the optional bond is present), (3) optionally reducing a compound of Formula IVA to a compound of Formula IVB (a compound of Formula IV in which the optional bond is absent) and (4) condensing the compound of Formula IV with an appropriate alkylating agent to form a compound of Formula I.

Step 1

Compounds of Formula V are prepared by proceeding as in Step 1 of Scheme I but replacing the substituted amine with ammonia.

Step 2

Compounds of Formula IVA are prepared by proceeding as in Step 2 of Scheme I but substituting a compound of Formula V for the compound of Formula II. Compounds of Formula IVB may be prepared by proceeding as described above for the hydrogenation of a compound of Formula IA but substituting a compound of Formula IVA.

Step 3

Compounds of Formula I are prepared by reacting, in the presence of a strong base, a compound of Formula IV with an alkylating agent of the formula $R^3L$ in which $R^3$ is as defined in the Summary of the Invention and L is a leaving group. The reaction is carried out under standard amide alkylating conditions (Luh, T.; Fung S. H. *Synth. Commun.* 1979, 9, 757) in an inert solvent at a reaction temperature of 20° C. to 100° C. Appropriate bases include sodium or sodium hydride and are usually employed in molar excess. Suitable solvents include tetrahydrofuran or N,N-dialkylformamides such as N,N-dimethylformamide.

Alternatively, alkylation may be accomplished via phase-transfer catalyst (PTC) techniques. Such techniques comprise carrying out the reaction in the presence of catalyst and in a liquid-liquid two phase solvent system (Gajda, T.; Zwierzak, A. *Synthesis, Communications* 1981, 1005), or preferably, in a solid-liquid system (Yamawaki, J.; Ando, T.; Hanafusa, T. *Chem, Lett.* 1981, 1143; Koziara, A.; ZaWasZki, S; Zwierzak, A. *Synthesis* 1979, 527, 549).

A liquid-liquid two-phase system is comprised of an aqueous phase consisting of a concentrated alkali hydroxide solution (e.g., 50% aqueous sodium hydroxide), an organic phase comprised of an inert water-immiscible organic solvent solvent, and an appropriate catalyst. A solid-liquid system consists of a powdered alkali hydroxide/alkali carbonate suspended in an organic solvent and catalyst.

The reaction is effected by adding slowly to a PTC system containing a compound of Formula IV an alkylating agent of the formula $R^3L$ until 10 to 50% in excess. The reaction mixture is kept at reflux until the reaction is complete. The mixture is then cooled to room temperature and the compound of Formula I is isolated by conventional methods. Suitable organic solvents include benzene, toluene, and the like. Appropriate catalysts include alumina coated with potassium fluoride and quaternary ammonium sulfates such as tetra-n-butyl-ammonium hydrogen sulfate and tricaprylylmethylammonium chloride.

A variation of Scheme II comprises converting a compound of Formula V to a compound of Formula II by one of the above described alkylation processes and then proceeding as in Step 2 of Scheme I to form a compound of Formula I.

Additional Processes

Compounds of Formula I in which substituent $R^1$ is $NH_2$ may be prepared by the reduction of a nitro substituent on the corresponding compound of Formula I; in which $R^1$ is alkoxy or dialkylamino, by substitution of a corresponding nitro or halo substituent; or in which $R^1$ is hydroxy, by the de-alkylation of a corresponding alkoxy substituent. Furthermore, compounds of Formula I in which $R^1$ is Cl, Br, I or $NO_2$ may be prepared by the introduction of such substituent onto a ring activated by an already present $R^1$ substituent such as $NH_2$, NHR, $NR_2$, OH or alkoxy; or in which $R^1$ is an acetamido substituent, by the acylation of a corresponding amino substituent. All of the additional processes described above may be performed by methods well known to one of ordinary skill in the art of organic synthesis.

Compounds of Formula I in which u is 1 (compounds of Formula I in which the cyclic amine portion of $R^3$ is in the N-oxide form) may be prepared by oxidation of the corresponding compound of Formula I in which u is 0, preferably the nonsalt form. The oxidation is carried out at a reaction temperature of approximately 0° C. with an appropriate oxidizing agent and in a suitable inert, organic solvent. Suitable oxidizing agents include peroxy acids such as trifluoroperacetic acid, permaleic acid, perbenzoic acid, peracetic acid, and m-chloroperoxybenzoic acid. Suitable solvents include halogenated hydrocarbons, e.g., dichloromethane. The oxidation of a compound of Formula I in which u is 0 to the corresponding N-oxide is described in Example 12. Alternatively, the compounds of Formula I in which u is 1 may be prepared using N-oxide derivatives of the starting materials or intermediates, which may be prepared in a similar manner.

Compounds of Formula I in which u is 0 (compounds of Formula I wherein the cyclic amine portion of $R^3$ is not in the N-oxide form) are also prepared by reduction of the corresponding compound of Formula I in which u is 1. The reduction is carried out under standard conditions with an appropriate reducing agent in a suitable solvent. The mixture is occasionally agitated while the reaction temperature is gradually increased over a range of 0° C. to 80° C. Appropriate reducing agents include sulfur, sulfur dioxide, triaryl phosphines (e.g., triphenyl phosphine), alkali borohydrides (e.g., lithium borohydride, sodium borohydride, etc.), phosphorus trichloride and tribromide. Suitable solvents include acetonitrile, ethanol or aqueous diozane.

As will be apparent to one of ordinary skill in the art, compounds of Formula I may be prepared as individual isomers or mixtures of isomers. Isomers which are diastereomers have distinct physical properties (e.g., melting points, boiling points, solubilities, reactivity, etc.) and are readily separated by taking advantage of these dissimilarities. For example, diastereomers can be separated by chromatography or, preferably, by separation/resolution techniques based upon differences in solubility. The separation of a single diastereomer of Formula I is described in Example 13.

Optical isomers can be separated by reacting the racemic mixture with an optically active resolving agent to form a pair of diastereomeric compounds. The isomers are then separated by any of the techniques described above for the separation of diastereomers and the pure optical isomer recovered, along with the resolving agent, by any practical means that would not result in racemization. While resolution of optical isomers can be carried out using covalent diastereomeric derivatives of compounds of Formula I, dissociable complexes are preferred, e.g., crystalline diastereomeric salts. Suitable resolving acids include tartaric acid, o-nitrotartranilic acid, mandelic acid, malic acid, the 2-arylpropionic acids in general, and camphorsulfonic acid.

Individual isomers of compounds of Formula I can also be separated by such methods as direct or selective crystallization or by any other method known to one of ordinary skill in the art. A more detailed description of the techniques applicable to the resolution of stereoisomers of compounds of Formula I can be found in Jean Jacques; Andre Collet; Samuel H. Wilen *Enantiomers, Racemates and Resolutions* 1981, John Wiley & Sons, Inc. Alternatively, individual isomers of compounds of Formula I can be prepared using the isomeric forms of the starting materials.

Compounds of Formula I are be converted to the corresponding acid addition salt with a pharmaceutically acceptable inorganic or organic acid. In addition, pharmaceutically acceptable salts may be formed when the acidic proton of $R^1$ hydroxy substituents present are capable of reacting with inorganic or organic bases. Inorganic and organic acids and bases suitable for the preparation of the pharmaceutically acceptable salts of compounds of Formula I are set forth in the definitions section of this application.

Compounds of Formula I in the acid addition salt form are converted to the corresponding free base by treatment with a suitable base such as ammonium hydroxide solution, sodium hydroxide or the like. Compounds of Formula I in which $R^1$ hydroxy substituents form salts are converted to the corresponding free base by treatment with a suitable acid such as hydrochloric acid.

Of the two processes for synthesizing compounds of Formula I described within this application, Scheme I is preferred. While compounds of Formula I may be synthesized by the process described in Scheme II, the alkylation step therein may require severe reaction conditions and is usually restricted to alkylation of unsubstituted amides with primary alkylating agents, e.g., $CH_3L$.

In summary, the processes for preparing the compounds of Formula I are:

(1) reacting a compound of Formula II with a formylating agent in the presence of a strong base and then acidifying to form a compound of Formula IA or reacting a compound of Formula IV with an alkylating agent of the formula $R^3L$ to form a compound of Formula I;

(2) optionally hydrogenating a compound of Formula IA to form a compound of Formula IB, (3) optionally reacting with or exchanging substituents present on a compound of Formula I to form an additional substituted compound of Formula I;

(4) optionally converting a salt of a compound of Formula I to the corresponding compound of Formula I;

(5) optionally converting a compound of Formula I to a corresponding pharmaceutically acceptable salt;

(6) optionally oxidizing a compound of Formula I in which u is 0 to form the corresponding N-oxide;

(7) optionally reducing the N-oxide of a compound of Formula I to the corresponding compound of Formula I in which u is 0; or (8) optionally separating a mixture of isomers of a compound of Formula I into a single isomer.

In any of the above last step processes, a reference to Formula I, IA, IB, II or IV refers to such Formulae wherein n, p, q, $R^1$, $R^2$, $R^3$, $R^4$, $R^5$, u, x, y, and z are as defined in their broadest definitions set forth in the Summary of the Invention, with the processes applying particularly well to the presently preferred embodiments.

EXAMPLE 1

2,6,7,8,9,9a-Hexahydrocyclohept[cd]isobenzofuran-2-one

The following is the preparation of a compound of Formula III in which n is 3;

both p and q are 0; and

X and Y are together oxo.

A solution of n-butyllithium/hexanes (2.5M, 32.0 mL, 80.0 mmol) was added in a dropwise fashion over five minutes to a heated solution of 5,6,7,8-tetrahydro-9H-benzocyclohepten-9-ol (4.03 g, 31.9 mmol) in hexane (100 mL). The mixture was maintained at reflux temperature and stirred for 20 hours. The mixture was then cooled to 10° C. and dry carbon dioxide was bubbled through for 5 hours, during which time a white precipitate formed. The reaction mixture was diluted with water (100 mL) and extracted with ethyl acetate. The aqueous solution was adjusted to pH 2.0 with concentrated hydrochloric acid while being stirred in an ice-water bath. The resulting precipitate was filtered and recrystallized from hexane to give 2,6,7,8,9,9a-hexahydrocyclohept[cd]isobenzofuran-2-one (2.63 g), m.p. 84°–85° C.

EXAMPLE 2

(RS)-N-(1-Azabicyclo[2.2.2]oct-3-yl)-4-indancarboxamide

The following is the preparation of a compound of Formula II via Scheme I, Step 1 in which n is 1;

p and q are 0; and $R^3$ is 1-azabicyclo[2.2.2]oct-3-yl.

A solution of (RS)-3-amino-1-azabicyclo[2.2.2]octane (1.51 g, 12 mmol) in toluene (20 mL) was added dropwise to a stirred solution of trimethylaluminum (12 mmol) in toluene (6 mL), so that the temperature did not exceed 10° C. The mixture was stirred for 30 minutes, and a solution of ethyl 4-indancarboxylate (2.16 g, 11.3 mmol) in toluene (20 mL) was gradually added. The reaction mixture was heated under reflux for 16 hours, then cooled to room temperature. The reaction mixture was added at 0° C. to aqueous hydrochloric acid (10%, 20 mL). After separation of the layers, the aqueous layer was made basic with 10N aqueous sodium hydroxide and extracted with ethyl acetate. The organic layer was dried with anhydrous potassium carbonate, filtered and evaporated to give 2.42 g (79%) of a white solid. A sample recrystallized from ethyl acetate gave (RS)-N-(1-azabicyclo[2.2.2]oct-3-yl)-4-indancarboxamide, m.p. 158°-158.5° C. Anal.: Calcd. for C₁₇H₂₂N₂O: C, 75.52; H, 8:20; N, 10.36. Found: C, 5.95; H, 8.22; N, 10.50.

Proceeding as in Example 2, but replacing (RS)-3-amino-1-azabicyclo[2.2.2]octane with (R)-3-amino-1-azabicyclo[2.2.2]octane gave (R)-N-(1-azabicyclo[2.2.2]oct-3-yl)-4-indancarboxamide.

Proceeding as in Example 2, but replacing (RS)-3-amino-1-azabicyclo[2.2.2]octane with (S)-3-amino-1-azabicyclo[2.2.2]octane gave (S)-N-(1-azabicyclo[2.2.2]oct-3-yl)-4-indancarboxamide, m.p. 159°-160° C.; [α]$_D^{25}$ −47.5° (c=0.4, CHCl₃).

Proceeding as in Example 2 the following are prepared:

N-(1-azabicyclo[2.2.2]oct-4-yl)-4-indancarboxamide;
N-(endo-9-methyl-9-azabicyclo[3.3.1]non-3-yl)-4-indancarboxamide;
N-(endo-8-methyl-8-azabicyclo[3.2.1]oct-3-yl)-4-indancarboxamide;
N-(exo-8-methyl-8-azabicyclo[3.2.1]oct-3-yl)-4-indancarboxamide;
N-(endo-1-azabicyclo[3.3.1]non-4-yl)-4-indancarboxamide;
(RS)-N-(1-azabicyclo[2.2.2]oct-3-yl)-4-indan-5-methoxycarboxamide;
(R)-N-(1-azabicyclo[2.2.2]oct-3-yl)-4-indan-5-methoxycarboxamide; and
(S)-N-(1-azabicyclo[2.2.2]oct-3-yl)-4-indan-5-methoxycarboxamide.

EXAMPLE 3

(S)-N-(1-Azabicyclo[2.2.2]oct-3-yl)-5,6,7,8-tetrahydro-1-naphthalenecarboxamide

The following is the preparation of a compound of Formula II via Scheme I, Step 1 in which n is 2;
p and q are 0; and
R³ is 1-azabicyclo[2.2.2]oct-3-yl.

A solution of 5,6,7,8-tetrahydro-1-naphthalenecarboxylic acid (Ofosu-Asante, K. and Stock, L. M., *J. Org. Chem.* 1986; 51: 5452) (2.06 g, 11.7 mmol), oxalyl chloride (1 mL, 11.7 mmol), and dimethylformamide (0.1 mL) in dichloromethane (20 mL) was stirred at room temperature for one hour. The mixture was then concentrated under reduced pressure, and the residue was dissolved in dichloromethane (20 mL). The resulting solution was added dropwise at 0° C. to a solution of (S)-3-amino-1-azabicyclo[2.2.2]octane (1.48 g, 11.7 mmol) in dichloromethane (20 mL). The solution was stirred at room temperature for 30 minutes, and the solvent was evaporated under vacuum. The residue was dissolved in water and washed with ethyl acetate. The aqueous layer was basified with NH₄OH and extracted with dichloromethane. The dichloromethane was dried with anhydrous potassium carbonate, filtered and then evaporated to afford 2.75 g of white crystals. A sample recrystallized from ethyl acetate/hexane gave (S)-N-(1-azabicyclo[2.2.2]oct-3-yl)-5,6,7,8-tetrahydro-1-naphthalenecarboxamide, m.p. 159°-160° C.; [α]$_D^{25}$ −42.1° (c=0.65, CHCl₃).

Proceeding as in Example 3, but replacing 5,6,7,8-tetrahydro-1-naphthalenecarboxylic acid with 5,6,7,8-tetrahydro-2-methoxy-1-naphthalenecarboxylic acid gave (S)-N-(1-azabicyclo[2.2.2]oct-3-yl)-5,6,7,8-tetrahydro-2-methoxy-1-naphthalenecarboxamide, m.p. 270°-271° C.

Proceeding as in Example 3, but replacing 5,6,7,8-tetrahydro-1-naphthalenecarboxylic acid with 4-chloro-5,6,7,8-tetrahydro-1-naphthalenecarboxylic acid gave (S)-4-chloro-N-(1-azabicyclo[2.2.2]oct-3-yl)-5,6,7,8-tetrahydro-1-naphthalenecarboxamide.

Proceeding as in Example 3, but replacing (S)-3-amino-1-azabicyclo[2.2.2]octane with 4-amino-1-azabicyclo[2.2.2]octane gave N-(1-azabicyclo[2.2.2]oct-4-yl)-5,6,7,8-tetrahydro-1-naphthalenecarboxamide.

Proceeding as in Example 3, but replacing (S)-3-amino-1-azabicyclo[2.2.2]octane with (RS)-3-amino-1-azabicyclo[2.2.2]octane gave (RS)-(1-azabicyclo[2.2.2]oct-3-yl)-5,6,7,8-tetrahydro-1-naphthalenecarboxamide.

Proceeding as in Example 3, but replacing (S)-3-amino-1-azabicyclo[2.2.2]octane with (R)-3-amino-1-azabicyclo[2.2.2]octane gave (R)-(1-azabicyclo[2.2.2]oct-3-yl)-5,6,7,8-tetrahydro-1-naphthalenecarboxamide.

Proceeding as in Example 3, but replacing (S)-3-amino-1-azabicyclo[2.2.2]octane with endo-9-methyl-9-azabicyclo[3.3.1]nonane gave N-(endo-9-methyl-9-azabicyclo[3.3.1]non-3-yl)-5,6,7,8-tetrahydro-1-naphthalenecarboxamide.

Proceeding as in Example 3, but replacing (S)-3-amino-1-azabicyclo[2.2.2]octane with endo-8-methyl-8-azabicyclo[3.2.1]octane gave N-(endo-8-methyl-8-azabicyclo[3.2.1]oct-3-yl)-5,6,7,8-tetrahydro-1-naphthalene carboxamide.

Proceeding as in Example 3, but replacing (S)-3-amino-1-azabicyclo[2.2.2]octane with exo-8-methyl-8-azabicyclo[3.2.1]octane gave N-(exo-8-methyl-8-azabicyclo[3.2.1]oct-3-yl)-5,6,7,8-tetrahydro-1-naphthalenecarboxamide.

Proceeding as in Example 3, but replacing (S)-3-amino-1-azabicyclo[2.2.2]octane with endo-1-azabicyclo[3.3.1]nonane gave N-(endo-1-azabicyclo[3.3.1]non-4-yl)-5,6,7,8-tetrahydro-1-naphthalenecarboxamide.

Proceeding as in Example 3 the following are prepared:

N-(exo-9-methyl-9-azabicyclo[3.3.1]non-3-yl)-5,6,7,8-tetrahydro-1-naphthalenecarboxamide; and
N-(exo-1-azabicyclo[3.3.1]non-4-yl)-5,6,7,8-tetrahydro-1-naphthalenecarboxamide.

EXAMPLE 4

N-(endo-9-Methyl-9-azabicyclo[3.3.1]non-3-yl)-5,6,7,8-tetrahydro-1-naphthalenecarboxamide The following is the preparation of a compound of Formula II via Scheme I, Step 1 in which n is 2;
each p, q and u is 0; and
R³ is
endo-9-methyl-9-azabicyclo[3.3.1]non-3-yl.

A solution of 5,6,7,8-tetrahydro-1-napthalene-carboxylic acid (571 mg, 3.24 mmol), oxalyl chloride (0.44 mL, 5.0 mmol), and dimethylformamide (0.05 mL) in dichloromethane (20 mL) was stirred at room temperature for one hour. The mixture was then concentrated under reduced pressure and the residue was dissolved in toluene (10 mL). The resulting solution was added dropwise to a stirred mixture of endo-3-amino-9-methyl-9-azabicyclo[3.3.1]nonane (500 mg, 3.24 mmol) and sodium carbonate (700 mg, 6.5 mmol) in water (5 mL) and toluene (25 mL). After 2 hours the mixture was diluted with ethyl acetate (100 mL). The layers were separated and the organic layer was dried with anhydrous magnesium sulfate, filtered, and concentrated under reduced pressure to afford 700 mg of white crystals. A sample recrystallized from ethyl acetate gave N-(endo-9-methyl-9-azabicyclo[3.3.1]non-3-yl)-5,6,7,8-tetrahydro-1-naphthalenecarboxamide, m.p. 166°–167° C.

EXAMPLE 5

(RS)-N-(1-Azabicyool[2.2.2]oct-3-yl)-5,6,7,8-tetrahydro-9H-benzocyclohepten-1-carboxamide The following is the preparation of a compound of Formula II via Scheme I, Step 1 in which
n is 3;
p and q are 0; and
$R^3$ is 1-azabicyclo[2.2.2]oct-3-yl.

A solution of (RS)-3-amino-1-azabicyclo[2.2.2]octane (1.00 g, 8 mmol)) in toluene (20 mL) was added dropwise to a stirred solution of trimethylaluminum (8 mmol) in toluene (10 mL), so that the temperature did not exceed 10° C. The mixture was stirred for 30 minutes, and a solution of 2,6,7,8,9,9a-hexahydrocyclohept[cd]isobenzofuran-2-one (1.25 g, 6.6 mmol) in toluene (10 mL) was gradually added. The reaction mixture was heated under under reflux 0.5 hours and then cooled to ambient temperature. Water was added gradually until a solid was precipitated, and the mixture was filtered. The solid was washed with ethyl acetate and the combined organic layer was evaporated to give (RS)-N-(1-azabicyclo[2.2.2]oct-3-yl)-9H-9-hydroxy-5,6,7,8-tetrahydrobenzocyclohepten-1-carboxamide (1.42 g, 68% yield). Crystallization from ethanolic hydrochloric acid gave (RS)-N-(1-azabicyclo[2.2.2]oct-3-yl)-9H-9-hydroxy-5,6,7,8-tetrahydrobenzocyclohepten-1-carboxamide hydrochloride, m.p. 239° C.

Reduction of (RS)-N-(1-azabicyclo[2.2.2]oct-3-yl)-9H-9-hydroxy-5,6,7,8-tetrahydrobenzocyclohepten-1-carboxamide (1.42 g, 4.5 mmol) in ethanolic hydrochloric acid (20 ml) with 20% palladium hydroxide on carbon (0.5 g) was carried out at 50 psi for 24 hours. The catalyst was removed by filtration and the filtrate was concentrated under reduced pressure. Purification of the product by column chromatography (10% methanol in methylene chloride and 1% ammonium hydroxide) gave (RS)-N-(1-azabicyclo[2.2.2]oct-3-yl)-5,6,7,8-tetrahydro-9H-benzocyclohepten-1-carboxamide (0.52 g, 39% yield).

Proceeding as in Example 5 the following are prepared:

N-(1-azabicyclo[2.2.2]oct-4-yl)-5,6,7,8-tetrahydro-1-naphthalenecarboxamide;

N-(endo-9-methyl-9-azabicyclo[3.3.1]non-3-yl)-5,6,7,8-tetrahydro-1-naphthalenecarboxamide;

N-(exo-9-methyl-9-azabicyclo[3.3.1]non-3-yl)-5,6,7,8-tetrahydro-1-naphthalenecarboxamide;

N-(endo-8-methyl-8-azabicyclo[3.2.1]oct-3-yl)-5,6,7,8-tetrahydro-1-naphthalene carboxamide;

N-(exo-8-methyl-8-azabicyclo[3.2.1]oct-3-yl)-5,6,7,8-tetrahydro-1-naphthalenecarboxamide;

N-(endo-1-azabicyclo[3.3.1]non-4-yl)-5,6,7,8-tetrahydro-1-naphthalenecarboxamide; and N-(exo-1-azabicyclo[3.3.1]non-4-yl)-5,6,7,8-tetrahydro-1-naphthalenecarboxamide.

EXAMPLE 6

(RS)-2-(1-Azabicylco[2.2.2]oct-3-yl)-1,2,4,5-tetrahydrocyclopent[de]isoquinolin-1-one The following is the preparation of a compound of Formula I via Scheme I, Step 2 in which
the optional bond is present;
n is 1;
each p, q and u is 0; and
$R^3$ is 1-azabicyclo[2.2.2]oct-3-yl.

A solution of (RS)-N-(1-azabicyclo[2.2.2]oct-3-yl)-4-indancarboxamide (2.07 g, 7.7 mmol), prepared as in Example 2, in dry tetrahydrofuran (100 mL) at −70° C. was treated with n-butyllithium (20 mmol). The reaction mixture was stirred at −10° C. for one hour, cooled to −70° C., and dimethylformamide (15 mmol) added in one portion. The reaction mixture was allowed to warm to room temperature over 1.5 hours, then cooled to 0° C. and acidified with 10% aqueous hydrochloric acid. The layers were separated, and the aqueous layer was washed with ethyl acetate, then made basic with 10N aqueous sodium hydroxide and extracted with ethyl acetate. The ethyl acetate was dried over anhydrous sodium sulfate, filtered, and evaporated to give 1.75 g (81% yield) of white crystals. A sample recrystallized from ethyl acetate gave (RS)-2-(1-azabicyclo[2.2.2]oct-3-yl)-1,2,4,5-tetrahydrocyclopent[de]isoquinolin-1-one, m.p. 146°–147° C. Anal.: Calcd. for $C_{18}H_{20}N_2O$: C, 77.11; H, 7.19; N, 9.99%. Found: C, 76.93; H, 7.23; N, 9.90%.

Crystallization from ethanolic hydrochloric acid gave the hydrochloride salt monoethanol adduct, m.p. 188°–190° C. Anal.: Calcd. for $C_{18}H_{20}N_2O$ HCl $C_2H_5OH$: C, 66.19; H, 7.50; N, 7.72%. Found: C, 66.08; H, 7.55; N, 7.66%.

Proceeding as in Example 6, but replacing (RS)-N-(1-aza-bicyclo[2.2.2]oct-3-yl)-4-indancarboxamide with (S)-N-(1-aza-bicyclo[2.2.2]oct-3-yl)-4-indancarboxamide, prepared as in Example 2, gave (S)-2-(1-azabicyclo[2.2.2]oct-3-yl)-1,2,4,5-tetrahydrocyclopent-[de]isoquinolin-1-one, m.p. 155.5°–156° C.; $[\alpha]_D^{25}+47.1°$ (c=0.41, $CHCl_3$). Anal.: Calcd. for $C_{18}H_{20}N_2O$: C, 77.11; H, 7.19, N, 9.99%. Found: C, 77.45; H, 7.12; N, 9.84%, and (S)-2-(1-azabicyclo[2.2.2]oct-3-yl)-1,2,4,5-tetrahydrocyclopent[de]isoquinolin-1-one hydrochloride m.p. >285° C.; $[\alpha]_D^{25}-12.8°$; Anal.: Calcd. for $C_{18}H_{20}N_{20}.HCl.0.5 H_2O$: C, 66.35; H,6.81; N, 8.59%. Found: C, 65.96; H, 6.86; N, 8.33%.

Proceeding as in Example 6, but replacing (RS)-N-(1-aza-bicyclo[2.2.2]oct-3-yl)-4-indancarboxamide with (R)-N-(1-aza-bicyclo[2.2.2]oct-3-yl)-4-indancarboxamide, prepared as in Example 2, gave (R)-2-(1-azabicyclo[2.2.2]oct-3-yl)-1,2,4,5-tetrahydrocyclopent-[de]isoquinolin-1-one and (S)-2-(1-azabicyclo[2.2.2]oct-3-yl)-1,2,4,5-tetrahydrocyclopent[de]isoquinolin-1-one hydrochloride.

EXAMPLE 7

(S)-2-(1-Azabicyclo[2.2.2]oct-3-yl)-2,4,5,6-tetrahydro-1H-benz[de]isoquinolin-1-one The following is the preparation of a compound of Formula I via Scheme I, Step 2 in which
the optional bond is present;
n is 2;
each p, q and u is 0; and
$R^3$ is 1-azabicyclo[2.2.2]oct-3-yl.

A solution of n-butyllithium in hexane (60 mmol) was added dropwise at −70° C. to a solution of (S)-N-(1-azabicyclo[2.2.2]oct-3-yl)-5,6,7,8-tetrahydro1-naphthalenecarboxamide (7.70 g, 21 mmol), prepared as in Example 3, in dry tetrahydrofuran (400 mL). The reaction mixture was stirred at −10° C. for one hour, cooled to −70° C., and dimethylformamide (100 mmol) added in one portion. The reaction mixture was allowed to warm to room temperature over 1.5 hours, then cooled to 0° C. and acidified with 10% aqueous hydrochloric acid. The layers were separated, and the aqueous layer was washed with ethyl acetate, then made basic with 10N aqueous sodium hydroxide and extracted with ethyl acetate. The ethyl acetate was dried over anhydrous sodium sulfate, filtered, and evaporated to give 7.58 g (95% yield) of (S)-2-(1-azabicyclo[2.2.2]oct-3-yl)-2,4,5,6-tetrahydro1H-benz[de]isoquinolin-1-one as white crystals; m.p. 117°–118° C.; $[\alpha]_D^{25}$ +43.2° (c=0.98, CHCl$_3$).

Crystallization from ethanolic hydrochloric acid gave 9.75 g of the hydrochloride salt monoethanol adduct as white crystals, m.p. >270° C., $[\alpha]_D^{25}$ −8.4° (c=2.4, H$_2$O). Anal.: Calcd. for C$_{19}$H$_{22}$N$_2$O HCl C$_2$H$_5$OH: C, 66.91; H, 7.75; N, 7.43%. Found: C, 66.77; H, 7.65; N, 7.27%.

Crystallization from isopropanolic hydrochloric acid gave the unsolvated hydrochloride salt.

Proceeding as in Example 7, but replacing (S)-N-(1-azabicyclo[2.2.2]oct-3-yl)-5,6,7,8-tetrahydro-1-naphthalenecarboxamide with (RS)-N-(1-azabicyclo[2.2.2]oct-3-yl)-5,6,7,8-tetrahydro-1-naphthalenecarboxamide, prepared as in Example 3, gave (RS)-2-(1-azabicyclo[2.2.2]oct-3-yl)-2,4,5,6-tetrahydro-1H-benz[de]isoquinolin-1-one hydrochloride m.p. 176°–177° C.

Proceeding as in Example 7, but replacing (S)-N-(1-azabicyclo[2.2.2]oct-3-yl)-5,6,7,8-tetrahydro-1-naphthalenecarboxamide with (R)-N-(1-azabicyclo[2.2.2]oct-3-yl)-5,6,7,8-tetrahydro-1-naphthalenecarboxamide, prepared as in Example 3, gave (R)-2-(1-azabicyclo[2.2.2]oct-3-yl)-2,4,5,6-tetrahydro-1H-benz[de]isoquinolin-1-one hydrochloride, m.p. >275° C., $[\alpha]_D^{25}$ +6.8° (c=2, H$_2$O).

Proceeding as in Example 7, but replacing (S)-N-(1-azabicyclo[2.2.2]oct-3-yl)-5,6,7,8-tetrahydro-1-naphthalenecarboxamide with (S)-N-(1-azabicyclo[2.2.2]oct-3-yl)-5,6,7,8-tetrahydro-2-methoxy-1-naphthalenecarboxamide, prepared as in Example 3, gave (S)-2-(1-azabicyclo[2.2.2]oct-3-yl)-2,4,5,6-tetrahydro-9-methoxy-1H-benz[de]isoquinolin-1-one.

Proceeding as in Example 7, but replacing (S)-N-(1-azabicyclo[2.2.2]oct-3-yl)-5,6,7,8-tetrahydro-1-naphthalenecarboxamide with (S)-N-(1-azabicyclo[2.2.2]oct-3-yl)-5,6,7,8-tetrahydro-4-chloro-1-naphthalenecarboxamide, prepared as in Example 3, gave (S)-2-(1-azabicyclo[2.2.2]oct-3-yl)-7-chloro-2,4,5,6-tetrahydro-1H-benz[de]isoquinolin-1-one.

EXAMPLE 8

2-(endo-9-Methyl-9-azabicyclo[3.3.1]non-3-yl)-2,4,5,6-tetrahydro-1H-benz[de]isoquinoli-1-one The following is the preparation of a compound of Formula I via Scheme I, Step 2 in which
the optional bond is present;
n is 2;
each p, q and u is 0; and
R$^3$ is endo-9-methyl-9-azabicyclo[3.3.1]non-3-yl.

A solution of n-butyllithium in hexane (5 mmol) was added dropwise at −70° C. to a solution of N-(endo-9-methyl-9-azabicyclo[3.3.1]non-3-yl)-5,6,7,8-tetrahydro-1-napthalenecarboxamide (0.7 g, 2.24 mmol), prepared as in Example 4, in dry tetrahydrofuran (25 mL). The reaction mixture was stirred at −10° C. for one hour, cooled to −70° C., and dimethylformamide (13 mmol) was added in one portion. The reaction mixture was allowed to warm to room temperature over 1.5 hours, then cooled to 0° C. and acidified with 10% aqueous hydrochloric acid. The layers were separated, and the aqueous layer was washed with ethyl acetate, then made basic with concentrated ammonium hydroxide and extracted with ethyl acetate (100 mL). The ethyl acetate was dried over anhydrous sodium sulfate, filtered, and evaporated to give 2-(endo-9-methyl-9-azabicyclo[3.3.1]non-3-yl)-2,4,5,6-tetrahydro-1H-benz[de]isoquinolone-1-one.

Crystallization from ethanolic hydrochloric acid gave the hydrochloride salt monoethanol adduct, m.p. 236° C. Anal.: Calcd. for C$_{21}$H$_{27}$ClN$_2$O H$_2$O: C, 66.92; H, 7.75; N, 7.43%. Found: C 66.45; H, 7.79; N, 7.32%.

Proceeding as in Example 8, but replacing N-(endo-9-methyl-9-azabicyclo[3.3.1]non-3-yl)-5,6,7,8-tetrahydro-1-napthalenecarboxamide with N-(1-azabicyclo[2.2.2]octan-4-yl)-5,6,7,8-tetrahydro-1-napthalenecarboxamide, prepared as in Example 3, gave 2-(1-azabicyclo[2.2.2]octan-4-yl)-2,4,5,6-tetrahydro-1H-benz[de]isoquinolin-1-one hydrochloride, m.p. 335°–337° C.

Proceeding as in Example 8, but replacing N-(endo-9-methyl-9-azabicyclo[3.3.1]non-3-yl)-5,6,7,8-tetrahydro-1-napthalenecarboxamide with N-(endo-8-methyl-8-azabicyclo[3.2.1]oct-3-yl)-5,6,7,8-tetrahydro-1-napthalenecarboxamide, prepared as in Example 3, gave 2-(endo-8-methyl-8-azabicyclo[3.2.1]oct-3-yl)-2,4,5,6-tetrahydro-1H-benz[de]isoquinolin-1-one hydrochloride, m.p. 269°–270°.

Proceeding as in Example 8, but replacing N-(endo-9-methyl-9-azabicyclo[3.3.1]non-3-yl)-5,6,7,8-tetrahydro-1-napthalenecarboxamide with N-(exo-8-methyl-8-azabicyclo[3.2.1]oct-3-yl)-5,6,7,8-tetrahydro-1-napthalenecarboxamide, prepared as in Example 3, gave 2-(exo-8-methyl-8-azabicyclo[3.2.1]oct-3-yl)-2,4,5,6-tetrahydro-1H-benz[de]isoquinolin-1-one hydrochloride, m.p. >270° C.

Proceeding as in Example 8, but replacing N-(endo-9-methyl-9-azabicyclo[3.3.1]non-3-yl)-5,6,7,8-tetrahydro-1-napthalenecarboxamide with N-(endo-1-azabicyclo[3.3.1]non-4-yl)-5,6,7,8-tetrahydro-1-napthalenecarboxamide, prepared as in Example 3 gave 2-(endo-1-azabicyclo[3.3.1]non-4-yl)-2,4,5,6-tetrahydro-1H-benz[de]isoquinolin-1-one hydrochloride, m.p. >360° C.

EXAMPLE 9

(RS)-2-(1-Azabicyclo[2.2.2]oct-3-yl)-1,2,4,5,6,7-hexahydrocyclohept[de]isoquinolin-1-one The following is the preparation of a compound of Formula I via Scheme I, Step 2 in which
the optional bond is present;
n is 3;
each p, q and u is 0; and
R$^3$ is 1-azabicyclo[2.2.2]oct-3-yl.

A solution of n-butyllithium in hexane (2.7 mmol) was added dropwise at −70° C. to a solution of (RS)-N-(1-azabicyclo[2.2.2]oct-3-yl)-5,6,7,8-tetrahydro-9H-benzocycloheptene-1-carboxamide (0.37 g, 1.2 mmol), prepared as in Example 5, in dry tetrahydrofuran (10 mL). The reaction mixture was stirred at −10° C. for one hour, cooled to −70° C., and dimethylformamide (1.5 mmol) was added in one portion. The reaction mixture was allowed to warm to room temperature over 1.5 hours, then cooled to 0° C. and acidified with 10% aqueous hydrochloric acid. The layers were separated, and the aqueous layer was washed with ethyl acetate, then made basic with aqueous ammonium hydroxide. The ethyl acetate was dried over anhydrous sodium sulfate, filtered, and the solvent was evaporated to give 0.15 g (40% yield) of (RS)-2-(1-azabicyclo-[2.2.2]oct-3-yl)-1,2,4,5,6,7-hexahydrocyclohept[de]isoquinolin-1-one as a foam. Crystallization from ethanolic hydrochloric acid gave the hydrochloride salt, m.p. >285° C.

Proceeding as in Example 9 the following are prepared: 2-(1-azabicyclo[2.2.2]oct-4-yl))-1,2,4,5,6,7-hexahydrocyclohept[de]isoquinolin-1-one; 2-(endo-9-methyl-9-azabicyclo[3.3.1]non-3-yl)-1,2,4,5,6,7-hexahydrocyclohept[de]isoquinolin-1-one;

2-(exo-9-methyl-9-azabicyclo[3.3.1]non-3-yl)-1,2,4,5,6,7-hexahydrocyclohept[de]isoquinolin-1-one;

2-(endo-8-methyl-8-azabicyclo[3.2.1]oct-3-yl)-1,2,4,5,6,7-hexahydrocyclohept[de]isoquinolin-1-one;

2-(exo-8-methyl-8-azabicyclo[3.2.1]oct-3-yl)-1,2,4,5,6,7-hexahydrocyclohept[de]isoquinolin-1-one 2-(endo-1-azabicyclo[3.3.1]non-3-yl)-1,2,4,5,6,7-hexahydrocyclohept[de]isoquinolin-1-one; and 2-(exo-1-azabicyclo[3.3.1]non-3-yl)-1,2,4,5,6,7-hexahydrocyclohept[de]isoquinolin-1-one.

EXAMPLE 10

(S)-2-(1-Azabicyclo[2.2.2]oct-3-yl)-2,3,3a,4,5,6-hexahydro-1H-benz[de]isoquinolin-1-one The following is the preparation of a diastereomeric mixture of a compound of Formula I via Scheme I, Step 3 in which the optional bond is absent;
n is 2;
p, q and u are 0; and
$R^3$ is 1-azabicyclo[2.2.2]oct-3-yl.

(S)-2-(1-azabicyclo[2.2.2]oct-3-yl)-2,4,5,6-tetrahydrobenz[de]isoquinolin-1-one (0.32 g, 1.1 mmol), prepared as in Example 3, in acetic acid (5 mL, containing 3 drops of 70% perchloric acid) was reduced with 20% palladium hydroxide on carbon (0.1 g) at 85° C. and 50 psi for 24 hours. The catalyst was removed by filtration and the filtrate was concentrated under reduced pressure. The residue was dissolved in water (10 mL), basified with ammonium hydroxide solution, and extracted with ethyl acetate. The ethyl acetate was dried over anhydrous potassium carbonate, filtered, and evaporated to give a diastereomeric mixture of (S)-2-(1-azabicyclo[2.2.2]oct-3-yl)-2,3,3a,4,5,6-hexahydro-1H-benz[de]isoquinolin-1-one (0.18 g 0.60 mmol) as a semisolid. Crystallization from a mixture of ethanolic hydrochloric acid, isopropanol, and ether gave 0.8 g of the hydrochloride salt as white crystals; m.p. >270° C. Anal.: Calcd. for $C_{19}H_{14}N_2O \cdot HCl \cdot 0.25\ H_2O$: C, 67.64; H, 7.62; N, 8.30%. Found: C, 67.38; H, 7.70; N, 8.10%.

Proceeding as in Example 10 other compounds of Formula I wherein the optional bond is absent can be prepared.

EXAMPLE 11

2-(1-Azabicyclo[2.2.2]oct-3S-yl)-2,3,3aS,4,5,6-hexahydro-1H-benz[de]isoquinolin-1-one The following is the preparation of a single diastereomer of Formula I in which the optional bond is absent;
n is 2;
p, q and u are 0; and
$R^3$ is 1-azabicyclo[2.2.2]oct-3-yl.

A diastereomeric mixture of 2-(1-azabicyclo[2.2.2]oct-3S-yl)-2,3,3a,4,5,6-hexahydro-1H-benz[de]isoquinolin-1-one (16.1 9, 54.0 mmol), prepared as in Example 10, was dissolved in ethyl alcohol (100 mL) and hydrochloric acid (59.4 mmol) was added. Crystallization from ethanolic hydrochloric acid and ether gave a diastereomeric mixture of 70% 2-(1-azabicyclo[2.2.2]oct-3S-yl)-2,3,3aS,4,5,6-hexahydro-1H-benz[de]isoquinolin-1-one hydrochloride (A) and 30% 2-(1-azabicyclo[2.2.2]oct-3S-yl)-2,3,3aR,4,5,6-hexahydro-1H-benz[de]isoquinolin-1-one hydrochloride (B) (10.6 g, 35.6 mmol).

Recrystallization of the 70/30% mixture from ethyl alcohol (100 mL) gave a diastereomeric mixture of 94% A and 6% B (6.24 g, 20.9 mmol), $[\alpha]_D^{25}$ −89.8° (c=0.3, H₂O).

Recrystallization of the 94/6% mixture from ethyl alcohol gave a disastereomeric mixture of 98.9% A and 1.1% B (4.58 g, 15.4 mmol), m.p. 296°–297° C., $[\alpha]_D^{25}$ −98.9° (c=0.53, H₂O).

EXAMPLE 12

(S)-2-(1-Azabicyclo[2.2.2]oct-3-yl)-2,4,5,6-tetrahydro-1H-benz[de]isoquinolin-1-one N-oxide The following is the preparation of a compound of Formula I via Scheme I, Step 3 in which the optional bond is present;
n is 2;
u is 1;
both p and q are 0; and
$R^3$ is 1-azabicyclo[2.2.2]oct-3-yl.

m-Chloroperoxybenzoic acid (0.82g, 4.7 mmol) was added in small portions at 0° C. to a solution of (S)-2-(1-azabicyclo[2.2.2]oct-3-yl)-2,4,5,6-tetrahydro-1-benz[de]isoquinolin-1-one, prepared as in Example 7, (1.16 g, 3.9 mmol) in dichloromethane (50 mL). The reaction mixture was stirred for additional 0.5 hour at 0° C. The solvent was removed under reduced pressure. Purification of the residue by column chromatography (10% methanol in dichloromethane and 1% ammonium hydroxide) gave the N-oxide of (S)-2-(1-azabicyclo[2.2.2]oct-3-yl)-2,4,5,6-tetrahydro-1H-benz[de]isoquinolin-1-one (0.75 g; 62% yield) as an amorphous solid; m.p. 73°–75° C.

Proceeding as in Example 10, other compounds of Formula I wherein u is 1 are prepared.

EXAMPLE 13

The following are representative pharmaceutical formulations containing a compound of Formula I.

ORAL FORMULATION

A representative solution for oral administration contains:

| Compound of Formula I | 100–1000 mg |
| --- | --- |
| Citric Acid Mono hydrate | 105 mg |
| Sodium Hydroxide | 18 mg |
| Flavouring | q.s. |
| Water | to 100 ml |

INTRAVENOUS FORMULATION

A representative solution for intravenous administration contains:

| | |
|---|---|
| Compound of Formula I | 10–100 mg |
| Dextrose Monohydrate | q.s. to make isotonic |
| Citric Acid Monohydrate | 1.05 mg |
| Sodium Hydroxide | 0.18 mg |
| Water for Injection | to 1.0 ml |

TABLET FORMULATION

A representative tablet form of a compound of Formula I may contain:

| | |
|---|---|
| Compound of Formula I | 1% |
| Microcrystalline cellulose | 73% |
| Stearic Acid | 25% |
| Colloidal Silica | 1% |

EXAMPLE 14

5-HT$_3$ Receptor Binding Assay

The following describes an in vitro assay for determining the 5-HT$_3$ receptor binding affinity of compounds of Formula I. The method is essentially that described by Kilpatrick et al., previously cited, which measures the affinity for 5-HT$_3$ receptors of the rat cerebral cortex radiolabelled with [$^3$H]quipazine.

Membranes are prepared from the cerebral cortices of rat brains homogenized in 50 mM Tris buffer (pH 7.4 at 4° C.) using a Polytron P10 tissue disrupter (setting 10, 2×10 sec bursts). The homogenate is centrifuged at 48,000×g for 12 min and the pellet obtained is washed, by resuspension and centrifugation, three times in homogenizing buffer. The tissue pellets are resuspended in the assay buffer, and are stored under liquid nitrogen until required.

The binding assays are conducted using a Tris-Krebs assay buffer of the following composition (mM): NaCl, 154; KCl, 5.4; KH$_2$PO$_4$, 1.2; CaCl$_2$.2H$_2$O, 2.5; MgCl$_2$, 1.0; glucose, 11; Tris, 10. Assays are conducted at 25° C. at 7.4 in a final volume of 0.25 ml. Zacopride (1.0 mM) is used to define the non-specific binding (NSB). 5-HT$_3$ receptors present in rat cortical membranes are labelled using 0.3–0.7 nM [$^3$H]quipazine (specific activity 50–66 Ci/mmol; New England Nuclear) in the presence of 0.1 mM paroxetine to prevent [$^3$H]quipazine binding to 5-HT uptake sites. The rat cortex membranes are incubated with [$^3$H]quipazine in the presence of 10 different concentrations of test compound ranging from $1 \times 10^{-12}$ to $1 \times 10^{-4}$ molar. Incubations are conducted for 45 min at 25° C. and are terminated by vacuum filtration over Whatman GF/B glass fiber filtersusing a Brandel 48 well cell harvester. After filtration the filters are washed for 8 sec with 0.1M NaCl. The filters are pretreated with 0.3% polyethyleneimine 18 hr prior to use in order to reduce filter binding of the radioligand. Radioactivity retained on the filters is determined by liquid scintillation counting.

The concentration of test compound producing 50% inhibition of radioligand binding is determined by an iterative curve fitting procedure. Affinities are expressed as the negative logarithm of the IC$_{50}$ value (pIC$_{50}$). Compounds of Formula I exhibit 5-HT$_3$ receptor binding affinity, i.e., pIC$_{50}$ values greater than 6.

EXAMPLE 15

5-HT$_3$ Receptor Antagonist Assay (Von Bezold-Jarisch Reflex)

The following describes an in vivo method for determining the 5-HT$_3$ antagonist activity of compounds of Formula I. The method is a modified version of that described by Butler et al., Cohen et al., and Fozard, all previously cited, in which the 5-HT$_3$ selective agonist 2-methyl-5-hydroxytryptamine (2-m-5-HT) is substituted for 5-HT.

Male Sprague-Dawley rats, 250–380 grams, are anesthetized with urethane (1.4 g/kg, i.p.). A tracheotomy is performed and a tube is inserted into the trachea to facilitate respiration. Jugular and femoral veins are canulated for intravenous administration of drug. The duodenum is canulated for intraduodenal administration of drug. Heart rate is monitored by Gould ECG/Biotech amplifiers. After at least a 30 min equilibration period and prior to administration of test compound, control responses to intravenous administration of 2-m-5-HT are determined and a minimal dose producing sufficient and consistent bradycardia is chosen.

Potency

Intravenous challenges to 2-m-5-HT are administered every 12 minutes. Either vehicle or test compound is administered intravenously 5 minutes before each challenge to 2-m-5-HT. Each successive administration of test compound is increased in dosage until responses to 2-m-5-HT are blocked.

Duration

Vehicle or test compound is administered intravenously or intraduodenally and subsequent challenges to 2-m-5-HT are administered at 5, 15, 30, 60, 120, 180, 240, 300 and, in some instances, 360, 420 and 480 minutes post dose.

For both potency and duration studies heart rate (beats/min) is recorded continuously for the duration of the study. Responses to 2-m-5-HT are represented by the peak decrease in heart rate. Effects of test compounds are represented as percent inhibition of the bradycardia induced by 2-m-5-HT. Data are analyzed by a one-way repeated measures ANOVA and followed by pairwise comparison to vehicle control using Fisher's LSD strategy. From a dose-response curve so constructed, an ID$_{50}$ value is obtained to represent the dose that inhibited 50% of the bradycardia induced by 2-m-5HT.

EXAMPLE 16

Ferret, Anti-Emesis Assay

The following describes the procedure for determining the intravenous (i.v.) effects of compounds of Formula I on cisplatin-induced emesis in ferrets.

Adult, male, castrated ferrets are allowed food and water ad libitum both prior to and throughout the testing period. Each animal is randomly chosen and anesthetized with a metofane/oxygen mixture, weighed and assigned to one of three test groups. While anesthetized an incision is made along the ventral cervical region approximately two to four centimeters in length. The jugular vein is then isolated and cannulated with a capped saline filled PE-50 polyethylene tubing. The cannula is exteriorized at the base of the skull and the incision closed with wound clips. The animals are then returned to their cages and allowed to recover from anesthesia prior to commencement of the study.

Vehicle or test compound is administered i.v. at 1.0 ml/kg and 1.0 mg/kg, respectively. Within 2.0 minutes of the administration of vehicle or test compound, cisplatin is injected i.v. at 1.0 mg/kg. The animals are then observed continuously for a 5 hour period and emetic responses (i.e., vomiting and/or retching) are recorded. For purposes of this example and that of Example 11, vomiting is defined as the successful evacuation of stomach contents and a single episode of retching is defined as rapid and successive efforts to vomit occurring within a one minute time period.

Emetic responses are represented as (1) time to onset of emesis, (2) total vomiting episodes and (3) total retching episodes. Means and standard deviations of the test groups are compared to those of the reference groups. Significance is determined by Student's t-test when comparing a single treatment group to the vehicle control or by Dunnett's comparative analysis when more than one treatment group is compared to a single vehicle.

Proceeding as in Example 8 but administering the test compounds by oral route, the anti-emetic effects of compounds of Formula I may be evaluated.

EXAMPLE 17

Dog, Anti-Emesis Assay

The following describes the procedure for determining the intravenous (i.v.) effects of compounds of Formula I on cisplatin-induced emesis in dogs.

Male and female dogs (6–15 kg) are fed one cup of dry dog food. One hour following feeding, cisplatin (cis-diamminedichloroplatinum) is administered i.v. at 3 mg/kg. Sixty minutes after the administration of cisplatin, either vehicle or test compound is injected i.v. at 0.1 ml/kg and 1.0 mg/kg, respectively. The dogs are then observed continuously for a 5 hour period and the emetic responses (i.e., vomiting and/or retching) are recorded.

Emetic responses are represented as (1) time to onset of emesis, (2) total vomiting episodes and (3) total retching episodes. Means and standard deviations of the test groups are compared to those of the reference groups. Significance is determined by Student's t-test when comparing a single treatment group to the vehicle control or by Dunnett's comparative analysis when more than one treatment group is compared to a single vehicle.

EXAMPLE 18

Prokinetic Assay

The following describes an in vivo method of determining the prokinetic activity of the compounds of Formula I by measuring the rate of gastric emptying of test meal in rats. The method is that described by Droppleman et al., previously cited.

Test meal is prepared by slowly adding 20 grams of cellulose gum (Hercules Inc., Wilmington, Del.) to 200 ml of cold distilled water that is being mixed in a Waring blender at approximately 20,000 rpm. Mixing continues until complete dispersion and hydration of the cellulose gum takes place (approximately 5 min). Three beef bouillon cubes are dissolved in 100 ml of warm water and then blended into the cellulose solution followed by 16 g of purified casein (Sigma Chemical Co., St. Louis, Mo.), 8 g of powdered confectioners sugar, 8 g of cornstarch, and 1 g of powdered charcoal. Each ingredient is added slowly and mixed thoroughly resulting in approximately 325 ml of a dark gray to black, homogenous paste. The meal is then refrigerated overnight during which time trapped air escapes. Prior to the assay the meal is removed from the refrigerator and allowed to warm to room temperature.

Mature (170 to 204 g) male Sprague-Dawley rats are deprived of food for 24 hours with water ad libitum. On the morning of the study each animal is weighed and randomly assigned to treatment groups consisting of ten animals per group. Each rat receives either vehicle, test compound or the reference standard metoclopramide by intraperitoneal injection. At 0.5 hours post injection 3.0 ml of test meal is orally administered to each rat with a 5.0 ml disposable syringe. Five test meal samples are weighed on an analytical balance and these weights are averaged to find a mean test meal weight. At 1.5 hours post injection each rat is sacrificed by carbon dioxide asphyxiation and the stomach is removed by opening the abdomen and carefully clamping and cutting the esophagus just below the pyloric sphincter. Taking care not to lose any of the its contents, each stomach is placed on a small, pre-weighed and correspondingly labeled 7 ml weigh boat and immediately weighed on an analytical balance. Each stomach is then cut open along the lesser curvature, rinsed with tap water, gently blotted dry to remove excess moisture and weighed. The amount of test meal remaining in the stomach is represented by the difference between the weight of the full stomach and the weight of the stomach empty. The difference between the amount of test meal remaining and the mean test meal weight represents the quantity of test meal that empties during the 1.5 hour post injection period.

Responses are represented as grams of meal emptied or percent change from control. Means and standard deviations of the test groups are compared to those of the reference groups. Significance is determined via Dunnett's t-test (Statistical Association Journal, December 1955, 1096–112).

EXAMPLE 19

Anxiolytic Behavior Assay

The following describes an in vivo method for determining anxiolytic activity of compounds of Formula I.

Naive male C5BI/6J mice, 18–20 g, are kept in groups of 10 mice in quarters controlled for sound, temperature and humidity. Food and water are available ad libitum. The mice are kept on a 12 hour light and 12 hour dark cycle, with lights on at 6:00 a.m. and off at 6:00 p.m. All experiments begin at least 7 days after arrival on site.

The automated apparatus for detecting changes in exploration is obtained from Omni-Tech Electronics Columbus Ohio and is similar to that of Crawley and Goodwin (1980), as described in Kilfoil et al., cited previously. Briefly, the chamber consists of a plexiglass box (44×21 ×21 cm), divided into two chambers by a black plexiglass partition. The partition dividing the two chambers contains a 13×5 cm opening through which the mouse can easily pass. The dark chamber has clear sides and a white floor. A fluorescent tube light (40 watt) placed above the chambers provides the only illumination. The Digiscan Animal Activity Monitor System RXYZCM16 (Omni-Tech Electronics) records the exploratory activity of the mice within the test chambers.

Prior to commencement of the study the mice are given 60 min to acclimatize to the laboratory environment. After a mouse receives an intraperitoneal (i.p.) injection of either test compound or vehicle it is returned to its home cage for a 15 min post-treatment period. The mouse is then placed in the center of the light chamber and monitored for 10 minutes.

Anxiolysis is seen as a general increase in exploratory activity in the lighted area. An increase in exploratory activity is relected by increased latency (the time for the mouse to move to the dark chamber when first placed in the center of the lighted area), increase in shuttle activity, increased or unaltered locomotor activity (number of grid lines crossed) and decreased time spent in the dark compartment.

EXAMPLE 20

Withdrawal Anxiety Assay

The following procedure describes a method to determine whether compounds of Formula I effect the anxiety that occurs after abruptly ceasing chronic treatment with drugs of abuse.

Naive male BKW mice (25-30 g) are caged in groups of ten in quarters controlled for sound, temperature and humidity. Food and water are available ad libitum. The mice are kept on a 12 hour light cycle and 12 hour dark cycle, with lights on at 6:00 a.m. and off at 6:00 p.m. All experiments begin at least 7 days after arrival on site.

Levels of anxiety are determined by the two-compartment exploratory model of Crawley and Goodwin (see Example 11). Anxiolysis is seen as a general increase in exploratory activity in the lighted area. An increase in exploratory activity is relected by increased latency (the time for the mouse to move to the dark chamber when first placed in the center of the lighted area), increased or unaltered locomotor activity (number of grid lines crossed), increased number of rears and decreased time spent in the dark compartment.

Increased exploratory activity in the lighted area is induced by treating the mice for 14 days with ethanol (8.0 % w/v in drinking water), nicotine (0.1 mg/kg, i.p., twice daily), diazepam (10.0 mg/kg, i.p., twice daily) or cocaine (1.0 mg/kg, i.p., twice daily). Anxiolysis is assessed 1, 3, 7 and 14 days after commencement of the drug regime. The treatment is abruptly ceased and exploratory activity in the lighted area is determined 8, 24 and 48 hours thereafter. Vehicle or test compounds are administered during the withdrawl phase by intraperitoneal injection. Responses are represented as inhibition of the decrease in anxiolytic behavior after the ethanol, cocaine, diazepam or nicotine treatment is ceased.

EXAMPLE 21

Cognitive Enhancement Assay

The following describes a model to determine the cognitive enhancing effects of compounds of Formula I.

Young adult and aged BKW mice are caged in groups of ten in quarters controlled for sound, temperature and humidity. Food and water are available ad libitum. The mice are kept on a 12 hour light cycle and 12 hour dark cycle, with lights on at 6:00 a.m. and off at 6:00 p.m. All experiments begin at least 7 days after arrival on site.

Levels of anxiety are determined by the two-compartment exploratory model of Crawley and Goodwin (see Example 11). Mice are exposed to the two-compartment test area over a 3 day period. The young mice habituate to the test area by day 3 and spend less time exploring the lighted area, whereas exploratory activity in the lighted area remains constant through day 3 for the aged mice. Exploratory activity is seen as latency (the time for the mouse to move to the dark chamber when first placed in the center of the lighted area), locomotor activity (number of grid lines crossed), number of rears and time spent in the lighted compartment. Vehicle or test compounds are administered to the aged mice by intraperitoneal injection. Cognitive enhancing effects in the aged rats are reflected by a decrease in exploratory activity by day 3.

We claim:

1. A compound of Formula I

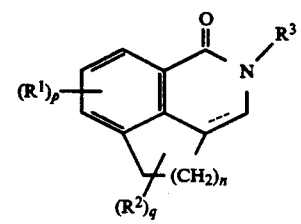

in which
the dashed line denotes an optional double bond;
n is 1, 2 or 3;
p is 0, 1, 2 or 3;
q is 0, 1 or 2;
each $R^1$ is independently selected from halogen, hydroxy, lower alkoxy, lower alkyl, nitro, amino, amino carbonyl, (lower alkyl)amino, di(lower alkyl)amino, and (lower alkanoyl)amino;
each $R^2$ is lower alkyl; and
$R^3$ is a group selected from Formulae (a), (b), (c) and (d):

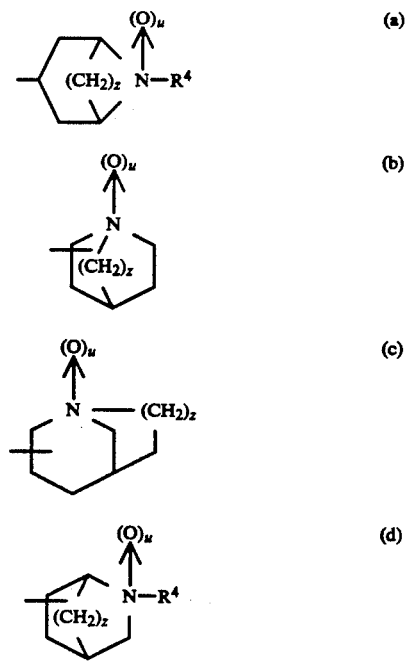

in which
u is 0 or 1;

z is 1, 2 or 3; and

R$^4$ is C$_{1-7}$ alkyl, C$_{3-8}$ cycloalkyl, C$_{3-8}$ cycloalkyl-C$_{1-2}$ alkyl, or a group (CH$_2$)$_t$R$^5$ where t is 1 or 2 and R$^5$ is thienyl, pyrrolyl, or furyl, each optionally further substituted by one or two substituents selected from C$_{1-6}$ alkyl, C$_{1-6}$ alkoxy, trifluoromethyl or halogen, or is phenyl optionally substituted by one or two substituents selected from C$_{1-4}$ alkoxy, trifluoromethyl, halogen, nitro, carboxy, esterified carboxy, and C$_{1-4}$ alkyl optionally substituted by hydroxy, C$_{1-4}$ alkoxy, carboxy, esterified carboxy or in vivo hydrolyzable acyloxy; the pharmaceutically acceptable salts, individual isomers, or mixtures of isomers thereof.

2. A compound of claim 1 in which both q and u are 0, p is 0, 1 or 2, each R' is independently selected from halogen, lower alkoxy or amino and R$^4$ is lower alkyl.

3. A compound of claim 2 in which p is 0, and R$^4$ is methyl.

4. A compound of claim 3 in which R$^3$ is one of the following groups:
1-azabicyclo[2.2.2]oct-3-yl;
1-azabicyclo-[2.2.2]oct-4-yl;
endo-9-methyl-9-azabicyclo[3.3.1]non-3-yl;
exo-9-methyl-9-azabicyclo[3.3.1]non-3-yl;
endo-8-methyl-8-azabicyclo[3.2.1]oct-3-yl;
exo-8-methyl-8-azabicyclo[3.2.1]oct-3-yl;
endo-1-azabicyclo[3.3.1]non-4-yl; or
exo-1-azabicyclo[3.3.1]non-4-yl.

5. A compound of claim 4 in which the optional bond is present.

6. A compound of claim 5 in which n is 1.

7. A compound of claim 6 in which R$^3$ is 1-azabicyclo[2.2.2]oct-3-yl, namely 2-(1-azabicyclo[2.2.2]oct-3-yl)-1,2,4,5-tetrahydrocyclopent[de]isoquinolin-1-one or a pharmaceutically acceptable salt thereof.

8. A compound of claim 7 which is (S)-2-(1-azabicyclo[2.2.2]oct-3-yl)-1,2,4,5-tetrahydrocyclopenta[de]isoquinolin-1-one or a pharmaceutically acceptable salt thereof.

9. A compound of claim 8 which is (S)-2-(1-azabicyclo[2.2.2]oct-3-yl)-1,2,4,5-tetrahydrocyclopenta[de]isoquinolin-1-one hydrochloride.

10. A compound of claim 6 in which R$^3$ is 8-methyl-8-azabicyclo[3.2.1]oct-3-yl, namely, 2-(8-methyl-8-azabicyclo[3.2.1]-oct-3-yl)-1,2,4,5-tetrahydrocyclopent[de]isoquinolin-1-one or a pharmaceutically acceptable salt thereof.

11. A compound of claim 10 which is 2-(endo-8-methyl-8-azabicyclo[3.2.1]-oct-3-yl)-1,2,4,5-tetrahydrocyclopent[de]isoquinolin-1-one or a pharmaceutically acceptable salt thereof.

12. A compound of claim 11 which is 2-(endo-8-methyl-8-azabicyclo[3.2.1]-oct-3-yl)-1,2,4,5-tetrahydrocyclopent[de]isoquinolin-1-one hydrochloride.

13. A compound of claim 5 in which n is 2.

14. A compound of claim 13 in which R$^3$ is 1-azabicyclo[2.2.2]oct-3-yl, namely 2-(1-azabicyclo[2.2.2]oct-3-yl)-2,4,5,6-tetrahydro-1H-benz[de]isoquinolin-1-one or a pharmaceutically acceptable salt thereof.

15. A compound of claim 14 which is (S)-2-(1-azabicyclo[2.2.2]oct-3-yl)-2,4,5,6-tetrahydro-1H-benz[de]isoquinolin-1-one or a pharmaceutically acceptable salt thereof.

16. A compound of claim 15 which is (S)-2-(1-azabicyclo[2.2.2]oct-3-yl)-2,4,5,6-tetrahydro-1H-benz[de]isoquinolin-1-one hydrochloride.

17. A compound of claim 14 which is (R)-2-(1-azabicyclo[2.2.2]oct-3-yl)-2,4,5,6-tetrahydro-1H-benz[de]isoquinolin-1-one or a pharmaceutically acceptable salt thereof.

18. A compound of claim 17 which is (R)-2-(1-azabicyclo[2.2.2]oct-3-yl)-2,4,5,6-tetrahydro-1H-benz[de]isoquinolin-1-one or hydrochloride.

19. A compound of claim 13 in which R$^3$ is 1-azabicyclo[2.2.2]oct-4-yl, namely 2-(1-azabicyclo[2.2.2]oct-4-yl)-2,4,5,6-tetrahydro-1H-benz[de]isoquinolin-1-one or a pharmaceutically acceptable salt thereof.

20. A compound of claim 13 in which R$^3$ is endo-9-methyl-9-azabicyclo[3.3.1]non-3-yl, namely 2-(endo-9-methyl-9-azabicyclo[3.3.1]non-3-yl)-2,4,5,6-tetrahydro-1H-benz[de]isoquinolin-1-one.

21. A compound of claim 13 in which R$^3$ is 8-methyl-8-azabicyclo[3.2.1]oct-3-yl, namely 2-(8-methyl-8-azabicyclo[3.2.1]oct-3-yl)-2,4,5,6-tetrahydro-1H-benz[de]isoquinolin-1-one or a pharmaceutically acceptable salt thereof.

22. A compound of claim 21 which is 2-(endo-8-methyl-8-azabicyclo[3.2.1]oct-3-yl)-2,4,5,6-tetrahydro-1H-benz[de]isoquinolin-1one or a pharmaceutically acceptable salt thereof.

23. A compound of claim 21 which is 2-(exo-8-methyl-8-azabicyclo[3.2.1]oct-3-yl)-2,4,5,6-tetrahydro-1H-benz[de]isoquinolin-1-one or a pharmaceutically acceptable salt thereof.

24. A compound of claim 13 in which R$^3$ is endo-1-azabicyclo[3.3.1]non-4-yl, namely 2-(endo-1-azabicyclo[3.3.1]non-4-yl)-2,3,5,6-tetrahydro-1H-benz[de]isoquinolin-1-one or a pharmaceutically acceptable salt thereof.

25. A compound of claim 5 in which n is 3.

26. The compound of claim 25 in which R$^3$ is 1-azabicyclo[2.2.2]oct-3-yl, namely 2-(1-azabicyclo[2.2.2]oct-3-yl)-1,2,4,5,6,7-hexahydrocyclohept[de]isoquinolin-1-one or a pharmaceutically acceptable salt thereof.

27. A compound of claim 4 in which the optional bond is absent.

28. A compound of claim 27 in which n is 1.

29. A compound of claim 27 in which n is 2.

30. A compound of claim 29 in which R$^3$ is 1-azabicyclo[2.2.2]oct-3-yl, namely 2-(1-azabicyclo-[2.2.2]oct-3-yl)-2,3,3a,4,5,6-hexahydro-1H-benz[de]isoquinolin-1-one.

31. A compound of claim 30 which is 2-(1-azabicyclo[2.2.2]oct-3S-yl)-2,3,3aS,4,5,6-hexahydro-1H-benz[de]isoquinolin-1-one or a pharmaceutically acceptable salt thereof.

32. A compound of claim 31 which is 2-(1-azabicyclo[2.2.2]oct-3S-yl)-2,3,3aS,4,5,6-hexahydro-1H-benz[de]isoquinolin-1-one hydrochloride.

33. A compound of claim 30 which is 2-(1-azabicyclo[2.2.2]oct-3S-yl)-2,3,3aR,4,5,6-hexahydro-1H-benz[de]isoquinolin-1-one or a pharmaceutically acceptable salt thereof.

34. A compound of claim 33 which is 2-(1-azabicyclo[2.2.2]oct-3S-yl)-2,3,3aR,4,5,6-hexahydro-1H-benz[de]isoquinolin-1-one hydrochloride.

35. A compound of claim 30 which is 2-(1-azabicyclo[2.2.2]oct-3R-yl)-2,3,3aS,4,5,6-hexahydro-1H-benz[de]isoquinolin-1-one a pharmaceutically acceptable salt thereof.

36. A compound of claim 35 which is 2-(1-azabicyclo[2.2.2]oct-3R-yl)-2,3,3aS,4,5,6-hexahydro-1H-benz[de]isoquinolin-1-one hydrochloride.

37. A compound of claim 30 which is 2-(1-azabicyclo-[2.2.2]oct-3R-yl)-2,3,3aR,4,5,6, -hexahydro-1H-benz-[de]isoquinolin-1-one or a pharmaceutically acceptable salt thereof.

38. A compound of claim 37 which is 2-(1-azabicyclo-[2.2.2]oct-3R-yl)-2,3,3aR,4,5,6-hexahydro-1H-benz-[de]isoquinolin-1-one hydrochloride.

39. A compound of claim 27 in which n is 3.

40. A pharmaceutical composition for treating a condition chosen from emesis, a gastrointestinal disorder treatable with prokinetic agents, anxiety/depressive state, and pain, which composition comprises a therapeutically effective amount of a compound of claim 1 in combination with a pharmaceutically acceptable carrier.

41. A method for treating a condition chosen from emesis, a gastrointestinal disorder treatable with prokinetic agents, anxiety/depressive state, and pain in an animal in need of such treatment, which method comprises administering a therapeutically effective amount of a compound of claim 1 to such animal.

42. A method of claim 41 in which the condition is a gastrointestinal disorder treatable with prokinetic agents.

43. A method of claim 41 in which the condition is pain.

44. A method of claim 41 in which the condition is anxiety/depressive state.

45. A method of claim 44 in which the condition is the side effects caused by withdrawal from an addictive substance.

46. A method of claim 41 in which the condition is emesis.

47. A method of claim 46 in which the condition is emesis in humans undergoing cancer treatment with a cytotoxic pharmaceutical agent or radiation at levels sufficient to induce emesis, or recovering from surgical anesthesia or undergoing drug therapy in general in which a significant side effect is emesis.

48. A method of claim 47 in which the compound is (S)-2-(1-azabicyclo[2.2.2]oct-3-yl)-2,4,5,6-tetrahydro-1H-benz[de]isoquinolin-1-one or a pharmaceutically acceptable salt thereof.

49. A method of claim 47 in which the compound is 2-(3S-1-azabicyclo-[2.2.2]oct-3-yl-2,3,3aS,4,5,6-hexahydro-1H-benz[de]isoquinolin-1-one or a pharmaceutically acceptable salt thereof.

50. A method of claim 42 in which the compound is (S)-2-(1-azabicyclo[2.2.2]oct-3-yl)-2,4,5,6-tetrahydro-1H-benz[de]isoquinolin-1-one.

* * * * *